US011517788B2

(12) United States Patent
Sano et al.

(10) Patent No.: US 11,517,788 B2
(45) Date of Patent: Dec. 6, 2022

(54) FINGER EXERCISE TRAINING MENU GENERATING SYSTEM, METHOD THEREOF, AND PROGRAM THEREOF

(71) Applicant: MAXELL, LTD., Kyoto (JP)

(72) Inventors: Yuko Sano, Tokyo (JP); Ying Yin, Beijing (CN); Tomohiko Mizuguchi, Kyoto (JP); Akihiko Kandori, Tokyo (JP); Mitsunobu Watanabe, Kyoto (JP); Hiroshi Shimizu, Kyoto (JP)

(73) Assignee: MAXELL, LTD., Kyoto (JP)

( * ) Notice: Subject to any disclaimer, the term of this patent is extended or adjusted under 35 U.S.C. 154(b) by 707 days.

(21) Appl. No.: 16/306,999

(22) PCT Filed: Mar. 7, 2017

(86) PCT No.: PCT/JP2017/009066
§ 371 (c)(1),
(2) Date: Dec. 4, 2018

(87) PCT Pub. No.: WO2017/212719
PCT Pub. Date: Dec. 14, 2017

(65) Prior Publication Data
US 2020/0222756 A1 Jul. 16, 2020

(30) Foreign Application Priority Data
Jun. 6, 2016 (JP) .............................. JP2016-112778

(51) Int. Cl.
*A63B 23/16* (2006.01)
*A63B 24/00* (2006.01)
*A63B 71/06* (2006.01)

(52) U.S. Cl.
CPC .......... *A63B 23/16* (2013.01); *A63B 24/0062* (2013.01); *A63B 24/0075* (2013.01);
(Continued)

(58) Field of Classification Search
CPC . A63B 23/16; A63B 24/0062; A63B 24/0075; A63B 71/0622;
(Continued)

(56) References Cited

U.S. PATENT DOCUMENTS 9,289,603 B1 * 3/2016 Giuffrida ............. A61B 5/4082
10,143,403 B2 * 12/2018 Ban ...................... A61B 5/1125
(Continued)

FOREIGN PATENT DOCUMENTS

JP 2006-187414 A 7/2006
JP 2012-176170 A 9/2012
(Continued)

OTHER PUBLICATIONS

Jonghin Park, et al., "A Training Support System for Finger Tapping Movements Using Magnetic Sensor", Collection of papers for lectures in the fortieth Chugoku and Shikoku Branch meeting, pp. 62-63, 2007. (Year: 2007).*
(Continued)

*Primary Examiner* — Robert P Bullington
*Assistant Examiner* — Stephen Alvesteffer
(74) *Attorney, Agent, or Firm* — Mattingly & Malur, PC

(57) ABSTRACT

A training apparatus is capable of generating and presenting a suitable training menu for finger exercise to maintain or improve a cognitive function and/or an exercise function of a human and supporting training of the human. The training apparatus includes a measuring apparatus and a terminal device. Analysis evaluating data based on measurement of the finger exercise including finger tapping is obtained, and the analysis evaluating data contains an evaluation value of an index item related to an exercise function of a user. A training menu for the user is generated based on the analysis evaluating data and contains a training item for the finger exercise. The index item includes at least one of an amount of exercise, endurance, rhythmicity, cooperativeness of both sides, or marker trackability. The training item includes an exercise to carry out the finger tapping in accordance with teaching information, stimulation, or a marker.

6 Claims, 29 Drawing Sheets

(52) U.S. Cl.
CPC .. *A63B 71/0622* (2013.01); *A63B 2071/0675* (2013.01); *A63B 2220/803* (2013.01); *A63B 2220/836* (2013.01); *A63B 2225/50* (2013.01)

(58) Field of Classification Search
CPC ...... A63B 2071/0675; A63B 2220/803; A63B 2220/836; A63B 2225/50; G09B 15/06; G09B 19/003; G06K 9/00536; G06K 9/00342; A61B 2505/09; A61B 5/4088; A61B 5/4082; A61B 5/6826; A61B 5/1124; A61B 5/1114; G01B 7/14
USPC ........................................................ 434/247
See application file for complete search history.

(56) References Cited

U.S. PATENT DOCUMENTS

| | | | | |
|---|---|---|---|---|
| 2010/0106060 A1* | 4/2010 | Tsuji | ................... | A61B 5/1101 |
| | | | | 600/587 |
| 2010/0228156 A1* | 9/2010 | Valero-Cuevas | ...... | A63B 23/16 |
| | | | | 600/587 |
| 2011/0054361 A1* | 3/2011 | Sakoda | ................ | A61B 5/4082 |
| | | | | 600/595 |
| 2011/0213277 A1* | 9/2011 | McNames | ............ | A61B 5/1124 |
| | | | | 600/595 |
| 2012/0157263 A1* | 6/2012 | Sivak | ................... | A61B 5/7475 |
| | | | | 482/4 |
| 2012/0196256 A1* | 8/2012 | Maeueler | ............... | G16H 20/30 |
| | | | | 434/247 |
| 2013/0060166 A1* | 3/2013 | Friedman | ............. | A61B 5/1125 |
| | | | | 600/595 |
| 2013/0143718 A1* | 6/2013 | Pani | ................... | A63B 21/4035 |
| | | | | 482/8 |
| 2016/0100788 A1 | 4/2016 | Sano et al. | | |
| 2017/0132947 A1 | 5/2017 | Maeda et al. | | |
| 2017/0296116 A1* | 10/2017 | McCarthy | .............. | A61B 5/486 |

FOREIGN PATENT DOCUMENTS

| | | |
|---|---|---|
| JP | 5330933 B2 | 10/2013 |
| JP | 2015-219881 A | 12/2015 |
| WO | 2015/037089 A1 | 3/2015 |
| WO | 2016/002885 A1 | 1/2016 |

OTHER PUBLICATIONS

International Search Report of PCT/JP2017/009066 dated May 30, 2017.

* cited by examiner

FIG. 9

ADMINISTRATION TABLE 50

| FEATURE AMOUNT CLASSIFICATION | IDENTIFICATION NUMBER | FEATURE AMOUNT PARAMETER [UNIT] | INDEX ITEM |
|---|---|---|---|
| DISTANCE | 1 | THE MAXIMUM AMPLITUDE OF DISTANCE [mm] | F (TRACKABILITY) H (AMPLITUDE CONTROL) |
| | 2 | TOTAL MOVING DISTANCE [mm] | A (AMOUNT OF EXERCISE) |
| | 3 | AVERAGE OF LOCAL MAXIMUM POINTS OF DISTANCE [mm] | F |
| | 4 | STANDARD DEVIATION OF LOCAL MAXIMUM POINTS OF DISTANCE [mm] | F, H |
| | 5 | SLOPE (ATTENUATION RATE) OF APPROXIMATE CURVE OF LOCAL MAXIMUM POINTS OF DISTANCE [mm/sec.] | B (ENDURANCE) |
| | 6 | COEFFICIENT OF VARIATION OF LOCAL MAXIMUM POINTS OF DISTANCE [-] | F, H |
| | 7 | STANDARD DEVIATION OF REGIONALLY LOCAL MAXIMUM POINTS OF DISTANCE [mm] | F, H |
| ... | ... | ... | ... |

FIG. 10

ADMINISTRATION TABLE 50

| INDEX ITEM ID | INDEX ITEM | TRAINING ITEM |
|---|---|---|
| A | AMOUNT OF EXERCISE | #1: Finger tap with faster speed and shorter cycle than those at the time of past training of finger tap by user |
| B | ENDURANCE | #2: Finger tap for duration time longer than duration time at the time of past training of finger tap by user. |
| C | RHYTHMICITY | #3: Accurate finger tap with pace slower than pace at the time of past training of finger tap by user or predetermined pace. |
| D | COOPERATIVENESS OF BOTH SIDES | #4: Finger tap for accurately both hands at the same time or alternately with pace slower than pace at the time of past training of finger tap by user or predetermined pace. |
| E | MARKER TRACKABILITY | #5: Finger tap to be accurately matched to position of marker with pace faster than pace at the time of past training of finger tap by user or predetermined pace. |
| F | MAGNITUDE OF EXERCISE | #6: Finger tap with opening/closing amplitude larger than opening/closing amplitude at the time of past training of finger tap by user or predetermined opening/closing amplitude. |
| G | WAVEFORM BALANCE | #7: Finger tap to be matched to teaching waveform of display screen with pace slower than that at the time of past training of finger tap by user or predetermined pace and opening/closing amplitude larger than that at the time of past training of finger tap by user or predetermined opening/closing amplitude. |
| H | AMPLITUDE CONTROL | #8: Finger tap while changing two or more kinds of opening/closing amplitude. |
| I | SPEED CONTROL | #9: Finger tap while changing two or more kinds of speed. |
| J | INDEPENDENT CONTROL OF BOTH HANDS | #10: Finger tap with different cycles or the like with respect to right and left hands by using both hands. |
| ... | ... | ... |

FIG. 15
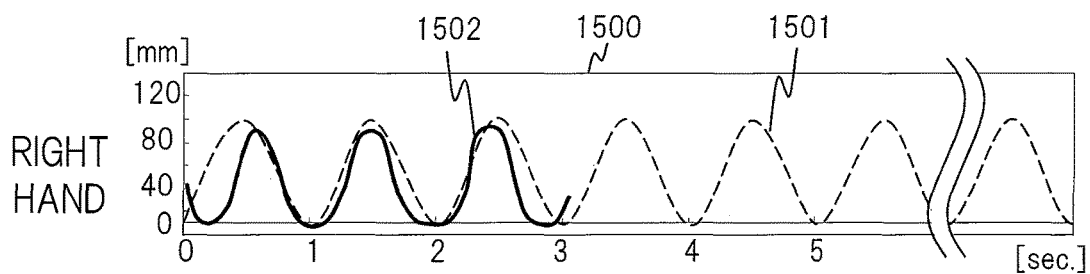
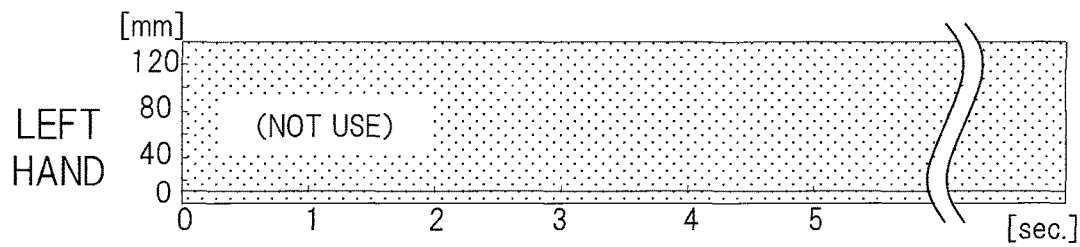
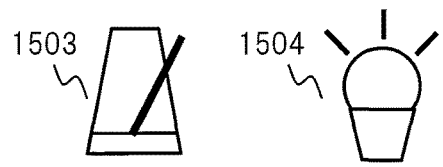

FIG. 16
TRAINING 2.  (A) AMOUNT OF EXERCISE
(BASE STRENGTHENING) Tap by one hand quickly (3 Hz).
Let's carry out finger tap by one hand quickly at pace of three times every one second. (Duration time: 30 seconds)
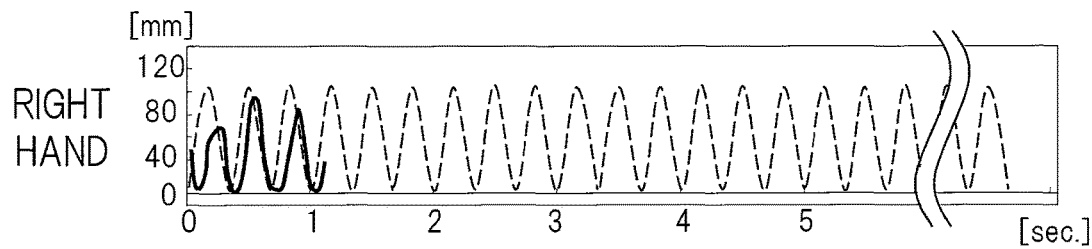
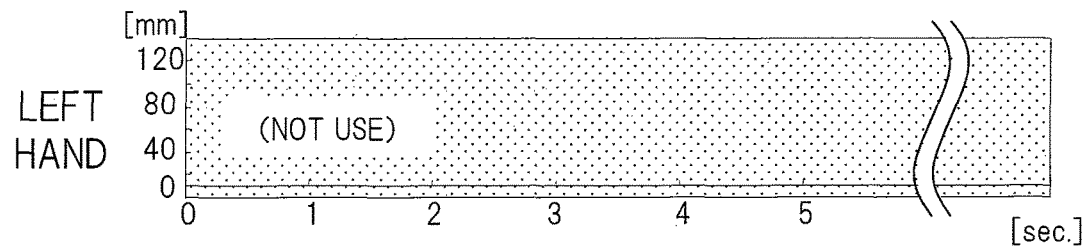
......

FIG. 19
TRAINING 5. (C) RHYTHMICITY + (A) AMOUNT OF EXERCISE + (D) COOPERATIVENESS OF BOTH SIDES
(FINISH) Accurately tap by both hands at the same time quickly (3 Hz).
Let's accurately carry out finger tap by both hands at the same time quickly at pace of three times every one second.
(Duration time: 30 seconds)
RIGHT HAND
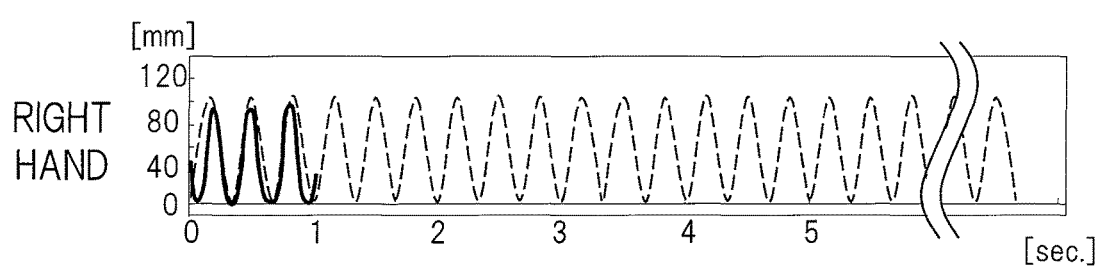
LEFT HAND
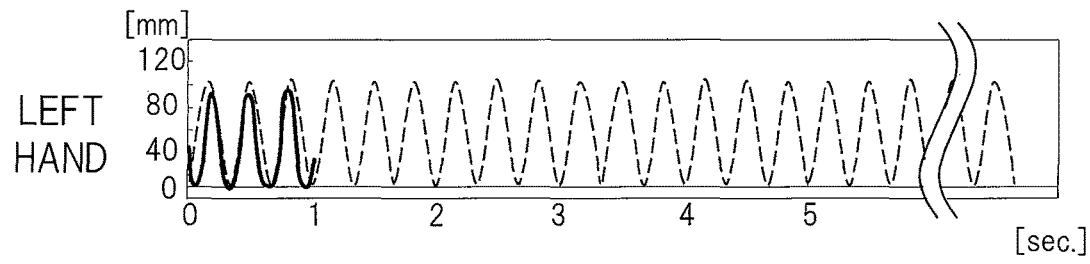
……

FIG. 23
(a) CROSS REACHING
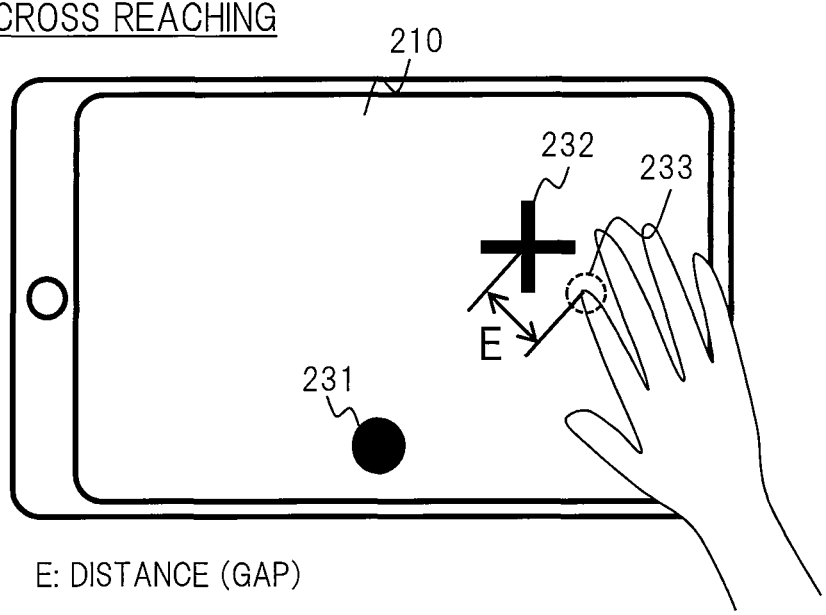
E: DISTANCE (GAP)
(b) CIRCLE REACHING
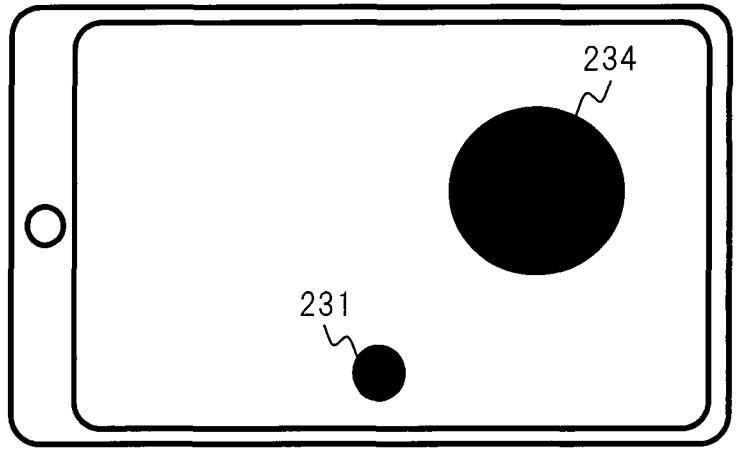

FIG. 24
(a) CONTINUOUS TOUCH BY ONE HAND
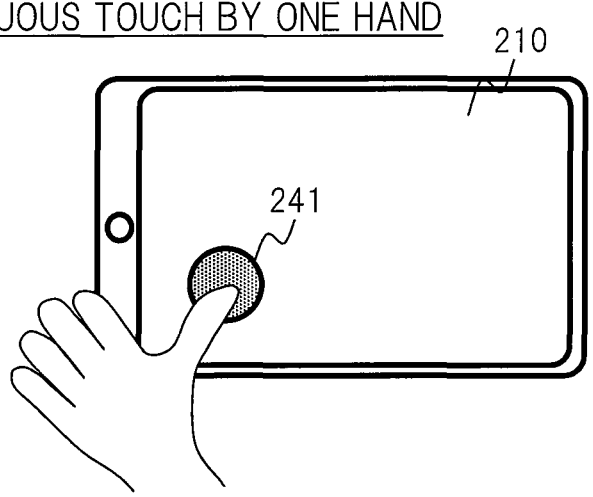
(b) CONTINUOUS TOUCH BY BOTH HANDS AT THE SAME TIME
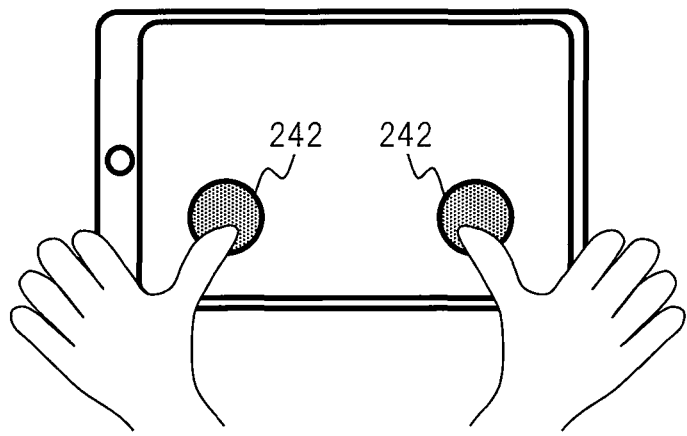

FIG. 25
(a) TAP BY ONE HAND
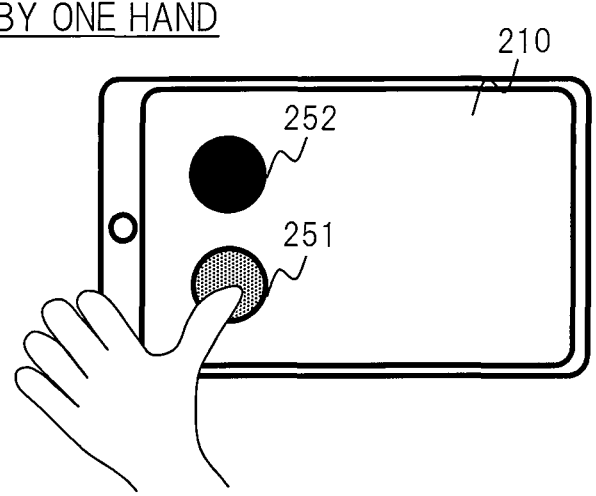
(b) TAP BY BOTH HANDS AT THE SAME TIME
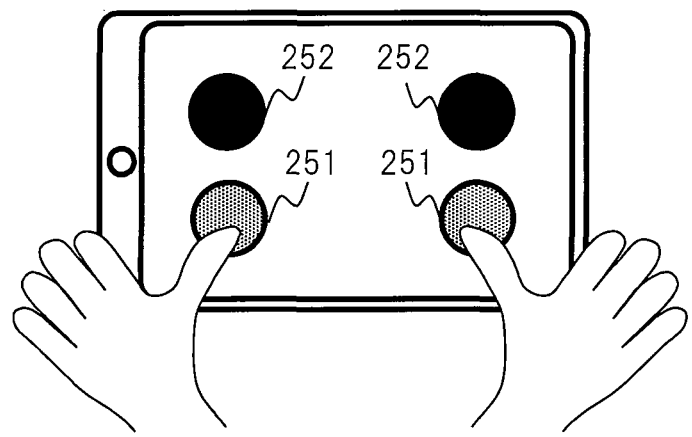

TAP BY FIVE FINGERS

FIG. 29

USER INFORMATION 41

| USER ID | FACILITIES ID | USER ID IN FACILITIES | SEX | AGE | DISEASE | SEVERITY SCORE |
|---|---|---|---|---|---|---|
| 0001 | H001 | ****** | MALE | 55 | DEMENTIA | ~ |
| 0002 | H002 | A**** | FEMALE | 35 | NO (HEALTHY) | ~ |
| 0003 | H003 | X**** | ... | ... | ... | ... |
| ... | ... | ... | ... | ... | ... | ... |

| SYMPTOM | EYESIGHT | HEARING | HISTORY INFORMATION | ... |
|---|---|---|---|---|
| ~ | 1.0 | NO PARTICULAR | A11 {DATE AND TIME, PRESENCE OR ABSENCE OF TRAINING, TASK MEASURED DATA, ANALYSIS EVALUATING DATA, TRAINING MENU DATA, TRAINING MEASURED DATA} A12 {DATE AND TIME, ···} | ... |
| ~ | 0.8 | NO PARTICULAR | A21 {DATE AND TIME, ···} | ... |
| ... | ... | ... | ... | ... |
| ... | ... | ... | ... | ... | ated
FINGER EXERCISE TRAINING MENU GENERATING SYSTEM, METHOD THEREOF, AND PROGRAM THEREOF

TECHNICAL FIELD

The present invention relates to a technique for information processing service. The present invention also relates to a technique for realizing training to maintain or improve a cognitive function and an exercise function of a human.

BACKGROUND ART

A system configured to simply evaluate a cognitive function and an exercise function of a human by means of measurement and analysis of an exercise of a finger of the human has been developed. For example, a test subject is caused to carry out a task of an exercise for finger tapping (hereinafter, referred to also as "finger tap" or the like) in a state where the test subject wears a sensor on his or her finger. The finger tapping is an exercise in which a state that two fingers are in contact with each other and a state that the two fingers are separated from each other are repeated by opening and closing the two fingers, for example. A measuring apparatus measures the exercise through the sensor. An analysis evaluating apparatus analyzes a property and a characteristic of the exercise on the basis of measured data, evaluates a cognitive function and an exercise function of the human, and outputs a result to a screen. As the property and the characteristic of the exercise, for example, the number of times of finger taps, an opening/closing distance, speed and the like are cited. For example, in a case where the number of times of finger taps by the test subject is smaller than an average value of the number of times of finger taps by healthy persons, an evaluation value of an index item such as an amount of an exercise of the test subject becomes smaller.

Moreover, an evaluation result by the system mentioned above can be used for estimate of possibility of disease of the test subject, evaluation of seriousness of the disease, and the like. The disease contains motor impairment. The motor impairment may include dementia, brain dysfunction such as Parkinson's disease, and the like.

As examples of a conventional technique regarding measurement of a finger exercise, analysis evaluation, estimate of disease and the like as described above, there are Japanese Patent No. 5,330,933B (Patent Document 1) and Non-Patent Document 1. Patent Document 1 describes that a feature amount of finger tapping by a test subject is compared with a feature amount of a healthy person and a value indicating a degree of motor impairment of the test subject is generated as an exercise function evaluating system.

Non-Patent Document 1 describes that a finger tapping exercise is quantified by using a magnetic sensor to evaluate an exercise function and a training support system capable of measuring and evaluating a finger tapping exercise is proposed.

RELATED ART DOCUMENTS

Patent Documents
    Patent document 1: Japanese Patent No. 5,330,933B
Non-Patent Documents
    Non-Patent document 1: "A Training Support System for Finger Tapping Movements Using Magnetic Sensor", Jonghin Park, et al., collection of papers for lectures in the fortieth Chugoku and Shikoku Branch meeting, pp. 62-63, 2007

SUMMARY OF THE INVENTION

Problems to be Solved by the Invention

It is thought that there is applicability of measurement of a finger exercise and analysis and evaluation thereof in a conventional system other than the estimate of disease based on evaluation of a cognitive function and/or an exercise function. For example, a finger tapping exercise can be utilized as rehabilitation and training for maintaining or improving the exercise function of people including not only patients but also healthy persons. It is thought that this is useful.

The conventional system does not consider that training of a user is supported by generating and presenting a suitable training menu for a finger exercise of the user, and a concrete training menu generating method and the like are not studied or examined. The conventional system does not also consider that a training menu suitable for each individual user is to be generated and continuous training for the user is to be supported.

Neither Patent Document 1 nor Non-Patent Document 1 describes generation, presentation and the like of a concrete training menu regarding the finger tapping exercise.

It is an object of the present invention to provide a technique capable of supporting training of a human by generating and presenting a suitable training menu for finger exercise to maintain or improve a cognitive function and an exercise function of the human with respect to information processing service.

Means for Solving the Problem

A representative embodiment of the present invention is a finger exercise training menu generating system configured to execute information processing to generate a training menu for a finger exercise of a human, which includes a configuration indicated below.

A finger exercise training menu generating system according to one embodiment is a finger exercise training menu generating system configured to execute information processing to generate a training menu for finger exercise including finger tapping, the finger exercise training menu generating system including: a training menu processor configured to: obtain analysis evaluating data based on measurement of the finger exercise, the analysis evaluating data containing an evaluation value of an index item related to an exercise function of a user; generate a training menu on a basis of the analysis evaluating data, the training menu containing training of a training item for the finger exercise; store training menu data; and present the training menu to the user, wherein the index item includes at least one of an amount of exercise, endurance, rhythmicity, cooperativeness of both sides, or marker trackability, and wherein the training item includes an exercise to carry out the finger tapping in accordance with teaching information, stimulation, or marker.

Effects of the Invention

According to a representative embodiment of the present invention, it is possible to support training of a human by generating and presenting a suitable training menu for finger exercise to maintain or improve a cognitive function and an exercise function of the human.

BRIEF DESCRIPTIONS OF THE DRAWINGS

FIG. 9 is a view showing configuration examples of the feature amount of an administration table according to the first embodiment;

FIG. 10 is a view showing a configuration example of an index item and a training item in the administration table according to the first embodiment;

FIG. 15 is a view showing a first training screen as an example of the display screen according to the first embodiment;

FIG. 16 is a view showing a second training screen as an example of the display screen according to the first embodiment;

FIG. 19 is a view showing a fifth training screen as an example of the display screen according to the first embodiment;

FIG. 23 is a view showing reaching as an exercise example according to the second embodiment;

FIG. 24 is a view showing continuous touch as an exercise example according to the second embodiment;

FIG. 25 is a view showing a tap in accordance with stimulation as an exercise example according to the second embodiment;

FIG. 29 is a view showing a configuration example of user information, which is management information of the server, according to the third embodiment.

DETAILED DESCRIPTION OF PREFERRED EMBODIMENTS

Figure 1:
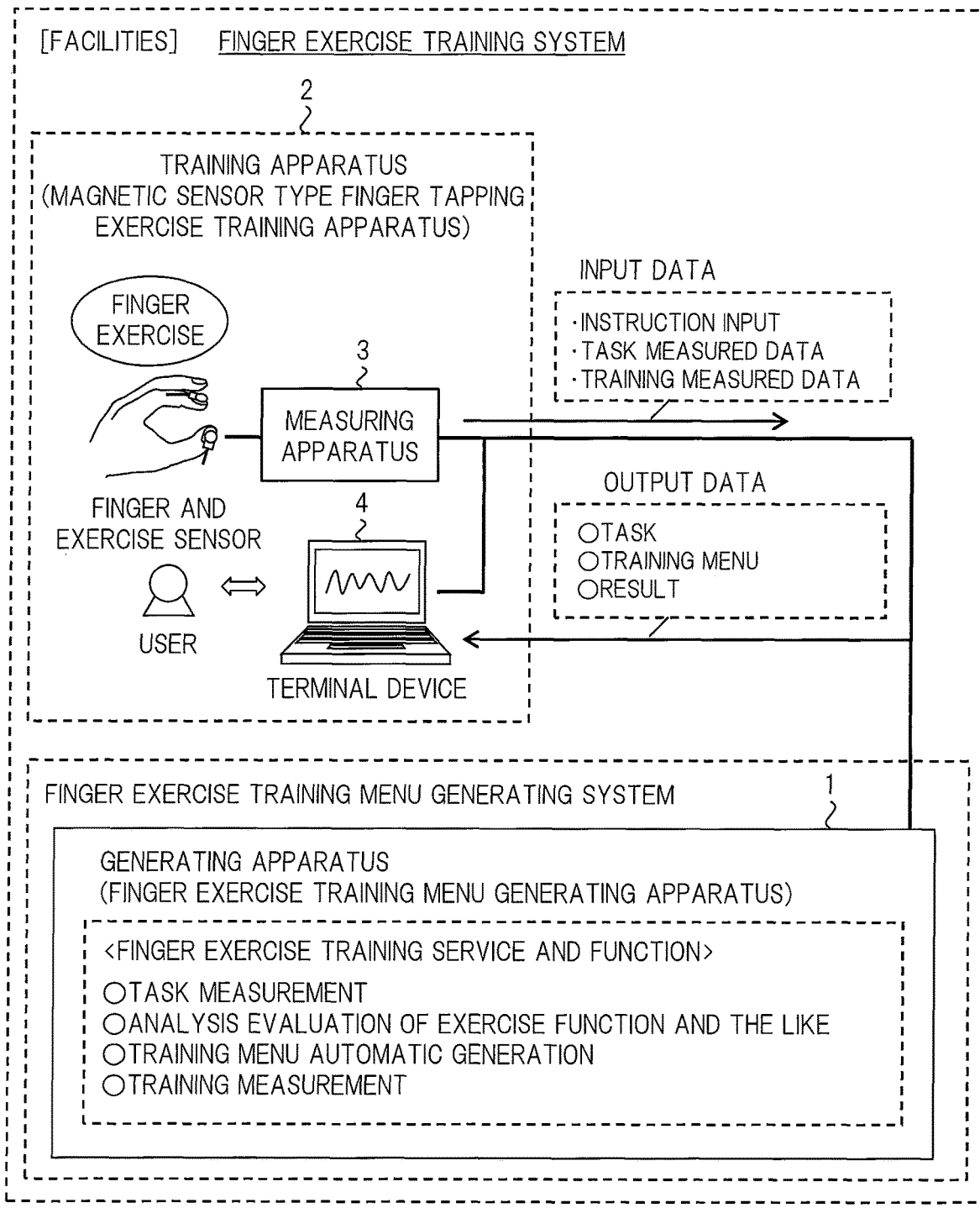
FIG. 1 is a view showing a configuration of a finger exercise training menu generating system according to a first embodiment of the present invention.

Hereinafter, embodiments of the present invention will be described in detail with reference to drawings. Note that the same reference numeral is assigned to the same element (or component) in all of Figures for explaining the embodiments and repeated explanation thereof is omitted.

First Embodiment

A finger exercise training menu generating system according to a first embodiment of the present invention will be described with reference to FIG. 1 to FIG. 19. The finger exercise training menu generating system according to the first embodiment has a function to support training of a user by generating and presenting a suitable training menu for a finger exercise of the user. The finger exercise training menu generating system according to the first embodiment is configured to generate a training menu suitable for each individual user, which contains training for a finger tapping exercise, and support continuous training for the user. This training allows an exercise function and the like of the user including not only a patient but also a healthy person to be maintained or improved.

[System (1)]

FIG. 1 shows a configuration of a finger exercise training system including a finger exercise training menu generating system according to the first embodiment. In the first embodiment, the finger exercise training system is provided in facilities. The finger exercise training system includes a generating apparatus 1 that constitutes the finger exercise training menu generating system and a training apparatus 2 that is a magnetic sensor type finger tapping exercise training apparatus. They are connected to each other through a communication line. The training apparatus 2 includes a measuring apparatus 3 and a terminal device 4. They are connected to each other through a communication line. A plurality of training apparatuses 2 may similarly be provided in the facilities.

The training apparatus 2 is an apparatus and a system of a type to measure a finger exercise by using a magnetic sensor type motion sensor. The motion sensor is connected to the measuring apparatus 3. The motion sensor is worn on a finger of a user. The measuring apparatus 3 measures a finger exercise through the motion sensor to obtain measured data containing a time-series waveform signal.

The terminal device 4 displays various kinds of information, which contain a training menu, for supporting training of the user on a display screen to receive an operational input by the user. In the first embodiment, the terminal device 4 is a personal computer (PC).

The generating apparatus 1 has a function to provide finger exercise training service as service by the information processing. The generating apparatus 1 has a task measuring function, an analysis evaluating function such as an exercise function, a training menu automatic generating function, a training measuring function, and the like as functions thereof. The task measuring function is a function to output a task for a finger exercise to the user, measure the task, and store task measured data. The analysis evaluating function is a function to carry out an analysis evaluating process of the task measured data to store analysis evaluating data, and present an evaluation result to the user. The training menu automatic generating function is a function to generate a training menu for the user from the analysis evaluating data to store training menu data, and present the training menu to the user. The training measuring function is a function to measure training of the training menu, store training measured data, and present a training result to the user.

For example, the instruction input, the task measured data, the training measured data and the like are inputted into the generating apparatus 1 as input data from the training apparatus 2. The generating apparatus 1 outputs the task, the training menu, a result, and the like, for example, as output data to the training apparatus 2.

The finger exercise training menu generating system according to the first embodiment is not limited to facilities such as a hospital and a test subject thereof, and can widely be applied to general facilities or persons. The measuring apparatus 3 and the terminal device 4 may be configured as the integral training apparatus 2. The measuring apparatus 3 and the generating apparatus 1 may be configured as an integral apparatus. The terminal device 4 and the generating apparatus 1 may be configured as an integral apparatus. The training apparatus 2 and the generating apparatus 1 may be configured as an integral apparatus.

[Finger Exercise Training Menu Generating Apparatus]

Figure 2:
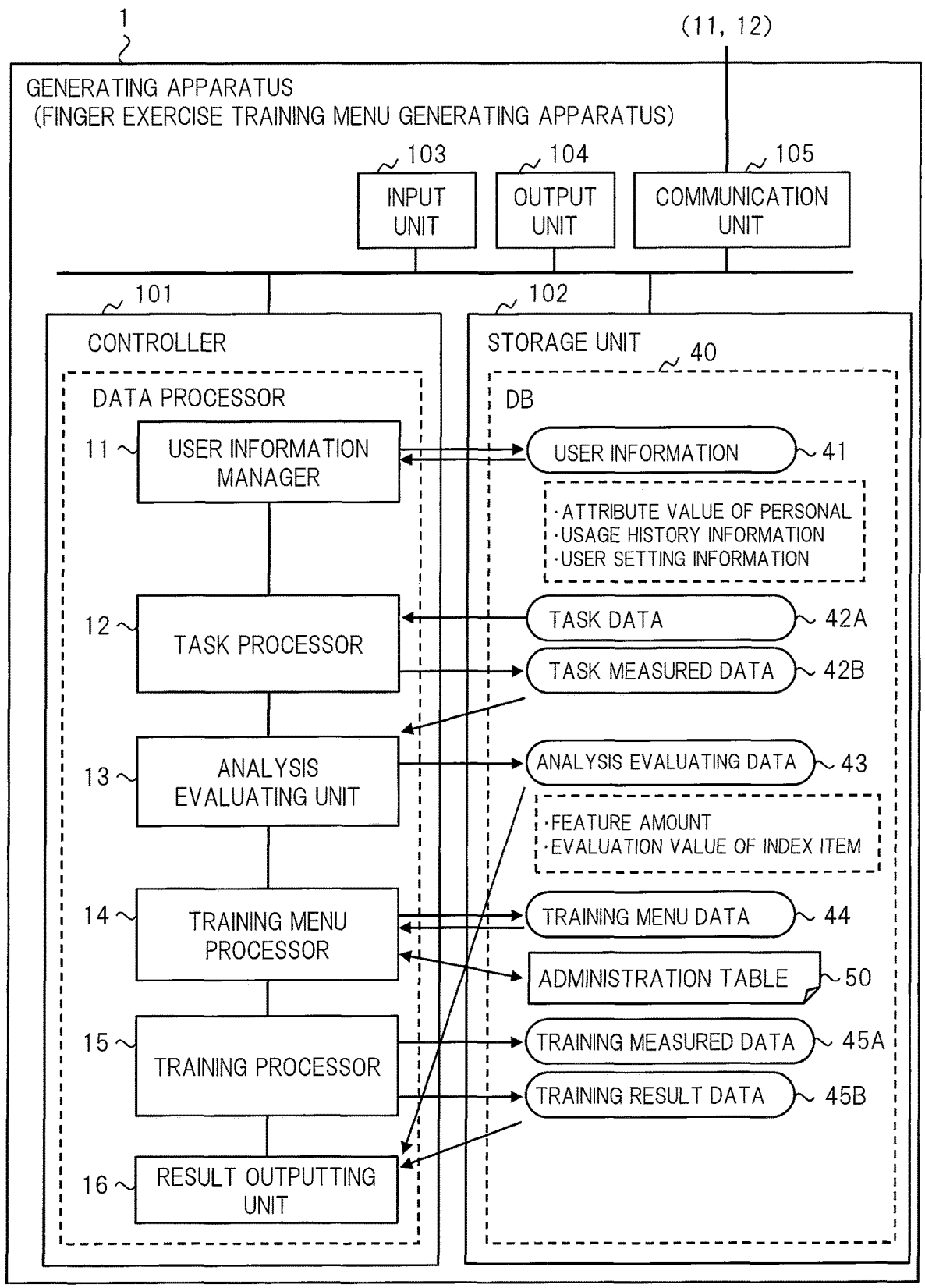
FIG. 2 is a view showing a configuration of a finger exercise training menu generating apparatus according to the first embodiment.

FIG. 2 shows a configuration of the generating apparatus 1 according to the first embodiment. The generating apparatus 1 includes a controller 101, a storage unit 102, an input unit 103, an output unit 104, a communication unit 105, and the like. They are connected to each other via a bus. The input unit 103 is a part to carry out an operational input by an administrator or the like of the generating apparatus 1. The output unit 104 is a part to carry out display of a screen to the administrator or the like of the generating apparatus 1 and the like. The communication unit 105 has a communication interface, and is a part to carry out communication processing with the measuring apparatus 3 and a terminal 4.

The controller 101 controls the whole generating apparatus 1, and is constructed by a CPU, a ROM, a RAM and the like. The controller 101 realizes a data processor to execute a finger exercise training menu generating process and the like on the basis of software program processing. The data processor of the controller 101 includes a user information manager 11, a task processor 12, an analysis evaluating unit 13, a training menu processor 14, a training processor 15, and a result outputting unit 16. The controller 101 realizes a function to input measured data from the measuring apparatus 3, a function to process and analyze the measured data, a function to output a control instruction to the measuring apparatus 3 and/or the terminal device 4, a function to output data for display to the terminal device 4, and the like.

The user information manager 11 carries out a process to register user information inputted by the user in user information 41 of a DB 40 and manage the user information 41, a process to confirm the user information 41 of the DB 40 when the user utilizes service and carries out training, and the like. The user information 41 contains an attribute value for each individual user, usage history information, user setting information, and the like. The attribute value is sex, age, or the like. The usage history information is information to manage a history that the user utilizes the service provided by the present system. The user setting information is setting information set by the user regarding the functions of the present service.

The task processor 12 is a part to execute a process regarding a task for analysis and evaluation of the exercise function and the like. In other words, the task is a predetermined finger exercise. The task processor 12 outputs a task onto a screen of the terminal device 4 on the basis of task data 42A of the DB 40. Further, the task processor 12 obtains task measured data measured by the measuring apparatus 3 to store them in the DB 40 as task measured data 42B.

The analysis evaluating unit 13 is apart to carry out analysis and evaluation regarding the cognitive function and the exercise function of the user on the basis of the task measured data 42B of the user. The analysis evaluating unit 13 carries out a process to extract a property and a feature amount of an exercise on the basis of the task measured data 42B, and a process to calculate an evaluation value of a predetermined index item such as an exercise function on the basis of the feature amount and the like. The analysis evaluating unit 13 stores analysis evaluating data 43, which is a result of the analysis evaluating process, in the DB 40.

The training menu processor 14 carries out a process to generate a training menu for the user on the basis of the analysis evaluating data 43 of the user and information of an administration table 50, and a process to output the training menu to the screen of the terminal device 4. The training menu processor 14 stores data on the generated training menu in the DB 40 as training menu data 44. The training menu processor 14 transmits the data on the training menu for the user to the terminal device 4 on the basis of the training menu data 44 of the DB 40, and causes the terminal device 4 to output the training menu to the screen.

The training processor 15 executes a process to obtain training measured data measured by the measuring apparatus 3 to store them in the DB 40 as training measured data 45A, a process to create training result data 45B on the basis of the training measured data 45A to store them in the DB 40, and the like. The training processor 15 utilizes the task processor 12 and/or the analysis evaluating unit 13 when the training result data 45B are to be created.

The result outputting unit 16 carries out a process to output evaluation result information and training result information of the user to the screen of the terminal device 4 on the basis of the analysis evaluating data 43 and the training result data 45B of the user. The analysis evaluating unit 13 and the training processor 15 carry out a screen outputting process in cooperation with the result outputting unit 16.

As the data and information stored in the DB 40 of the storage unit 102, there are the user information 41, the task data 42A, the task measured data 42B, the analysis evaluating data 43, the training menu data 44, the training measured data 45A, the training result data 45B, the administration table 50, and the like. The controller 101 holds the administration table 50 in the storage unit 102 and manages the held administration table 50. The administrator is allowed to set the content of the administration table 50. The information on the feature amount, the index item, and the training item is set to the administration table 50.

[Measuring Apparatus]

Figure 3:
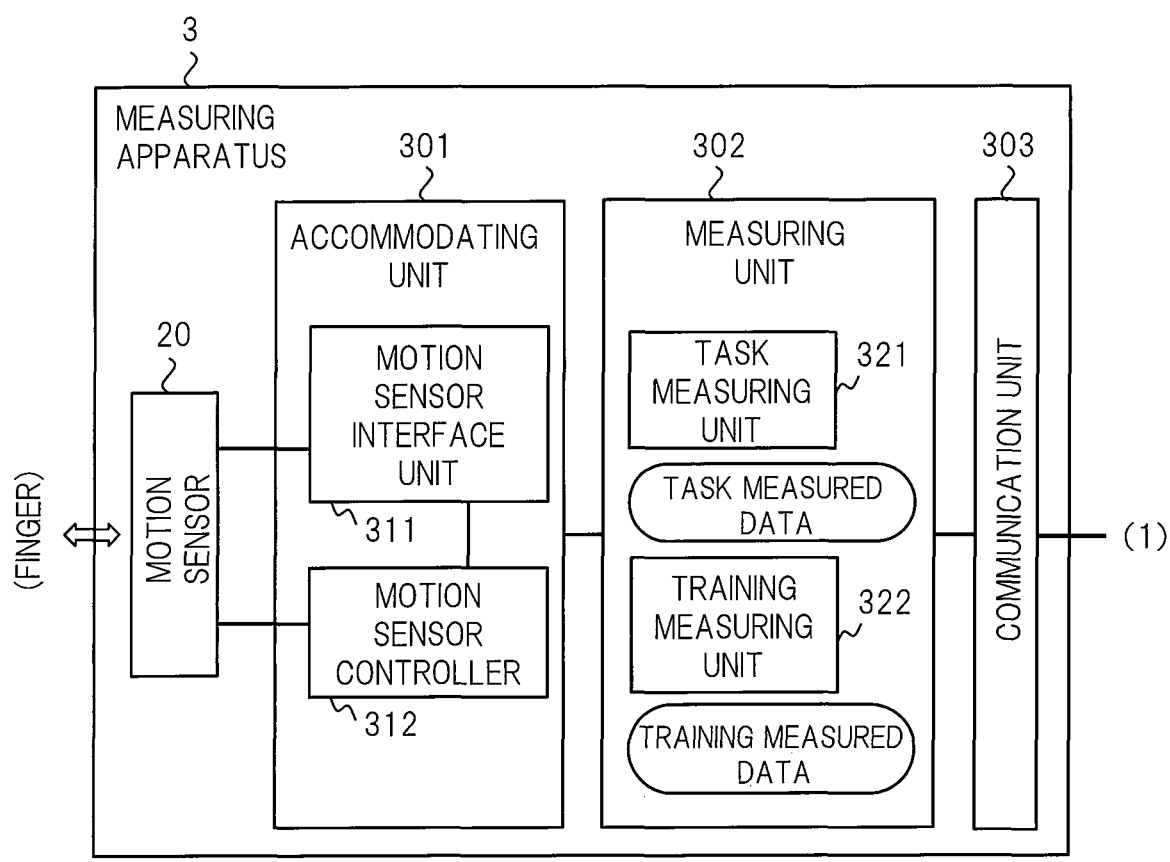
FIG. 3 is a view showing a configuration of a measuring apparatus according to the first embodiment.

FIG. 3 shows a configuration of the measuring apparatus 3 according to the first embodiment. The measuring apparatus 3 includes a motion sensor 20, an accommodating unit 301, a measuring unit 302, a communication unit 303 and the like. The accommodating unit 301 includes a motion sensor interface unit 311 to which the motion sensor 20 is connected and a motion sensor controller 312 that controls the motion sensor 20. The measuring unit 302 measures a waveform signal through the motion sensor 20 and the accommodating unit 301, and outputs the waveform signal as measured data. The measuring unit 302 includes a task measuring unit 321 configured to obtain the task measured data and a training measuring unit 322 configured to obtain the training measured data. The communication unit 303 has a communication interface, and communicates with the generating apparatus 1 to transmit the measured data to the generating apparatus 1. The motion sensor interface unit 311 includes an analog-to-digital converter circuit, and converts an analog waveform signal detected by the motion sensor 20 into a digital waveform signal by means of sampling. The digital waveform signal is inputted into the motion sensor controller 312.

Note that the finger exercise training system may be a configuration in which each of the measured data is held in storage unit in the measuring apparatus 3, or a configuration in which each of the measured data is not held in the measuring apparatus 3 but is held only in the generating apparatus 1.

[Terminal Device]

Figure 4:
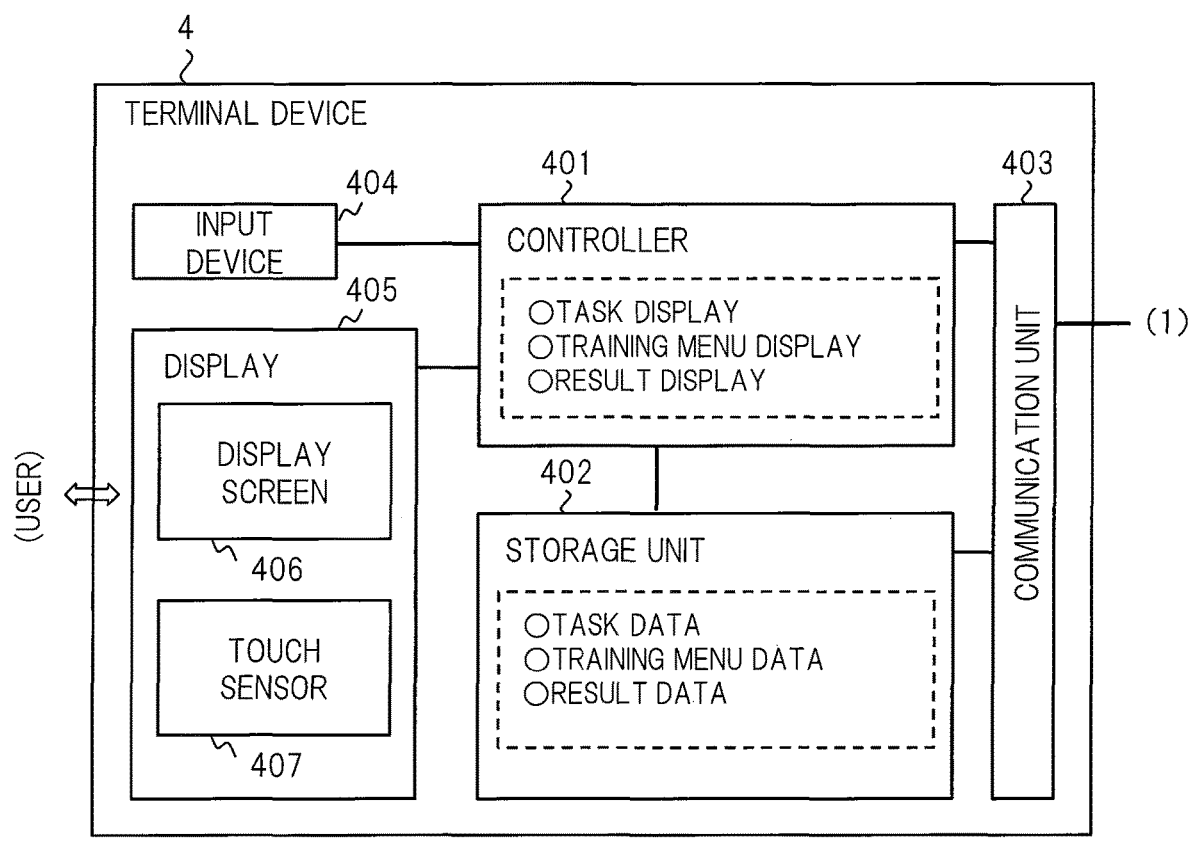
FIG. 4 is a view showing a configuration of a terminal device according to the first embodiment.

FIG. 4 shows a configuration of the terminal device 4 according to the first embodiment. The terminal device 4 includes a controller 401, a storage unit 402, a communication unit 403, an input device 404, and a display 405. The controller 401 carries out task display, training menu display, result display, user instruction input reception and the like as control processes based on software program processing. Task data, training menu data, result data, and the like obtained from the generating apparatus 1 are stored in the storage unit 402. The communication unit 403 has a communication interface, and communicates with the generating apparatus 1 to receive various kinds of data from the generating apparatus 1 and transmit user instruction input information and the like to the generating apparatus 1. As the input device 404, there are a keyboard, a mouse and the like. The display 405 displays various kinds of information on a display screen 406. Note that the display 405 may be used as a touch panel.

[Finger, Motion Sensor, and Measurement of Finger Tapping Exercise]

Figure 5:
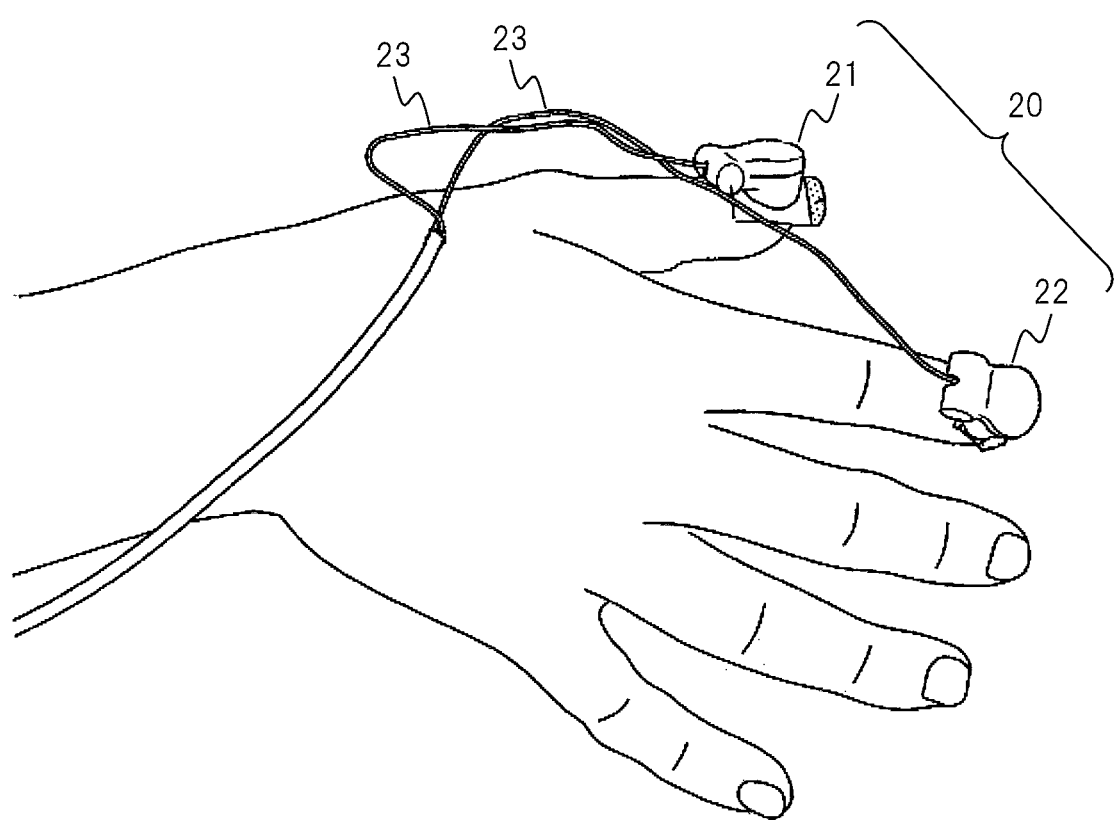
FIG. 5 is a view showing a motion sensor worn on fingers according to the first embodiment.

FIG. 5 shows a state where a magnetic sensor that is the motion sensor 20 is worn on fingers of the user. The motion sensor 20 includes a transmitting coil unit 21 and a receiving coil unit 22, which are coil portions mating a pair through signal lines 23 connected to the measuring apparatus 3. The transmitting coil unit 21 generates a magnetic field, and the receiving coil unit 22 detects the magnetic field. In the example of FIG. 5, on a right hand of the user, the transmitting coil unit 21 is worn in the vicinity of a nail of a thumb, and the receiving coil unit 22 is worn in the vicinity of a nail of a forefinger. The fingers on which the transmitting and receiving coil units 21, 22 are to be worn can be changed into other fingers. A portion to which each of them is to be worn is not limited to the vicinity of the nail thereof, and can be any other portion of the corresponding finger.

As shown in FIG. 5, it becomes a state where the motion sensor 20 is worn on target fingers of the user, for example, two fingers of a left hand, that is, a thumb and a forefinger. The user carries out a finger tapping that is an exercise to repeat opening/closing of the two fingers in the state. In the finger tapping, an exercise to change between a state that the two fingers are closed, that is, a state that tips of the two fingers contact with each other and a state that the two fingers are opened, that is, a state that the tips of the two fingers are opened is carried out. A distance between the coil portions of the transmitting coil unit 21 and the receiving coil unit 22, which corresponds to a distance between the tips of the two fingers, is changed with the exercise. The measuring apparatus 3 measures a waveform signal based on a change in a magnetic field occurring between the transmitting coil unit 21 and the receiving coil unit 22 of the motion sensor 20.

A finger tapping exercise includes each of the following kinds in detail. As the exercises, one-hand free run, one-hand metronome, both hands free run at the same time, both hands free run alternately, both hands metronome at the same time, both hands metronome alternately and the like may be cited. The one-hand free run indicates that a finger tap is carried out by one hand of the two fingers as quickly as possible any number of times. The one-hand metronome indicates that a finger tap is carried out by one hand of the two fingers so as to be matched to stimulation at a fixed pace. The both hands free run at the same time indicates that a finger tap is carried out by the two fingers of the left hand and the two fingers of the right hand at the same timing. The both hands free run alternately indicates that a finger tap is carried out by the two fingers of the left hand and the two fingers of the right hand at alternate timing. The exercises described above such as one-hand free run can be set as a task or training.

[Motion Sensor Controller and Finger Tapping Measurement]

Figure 6:
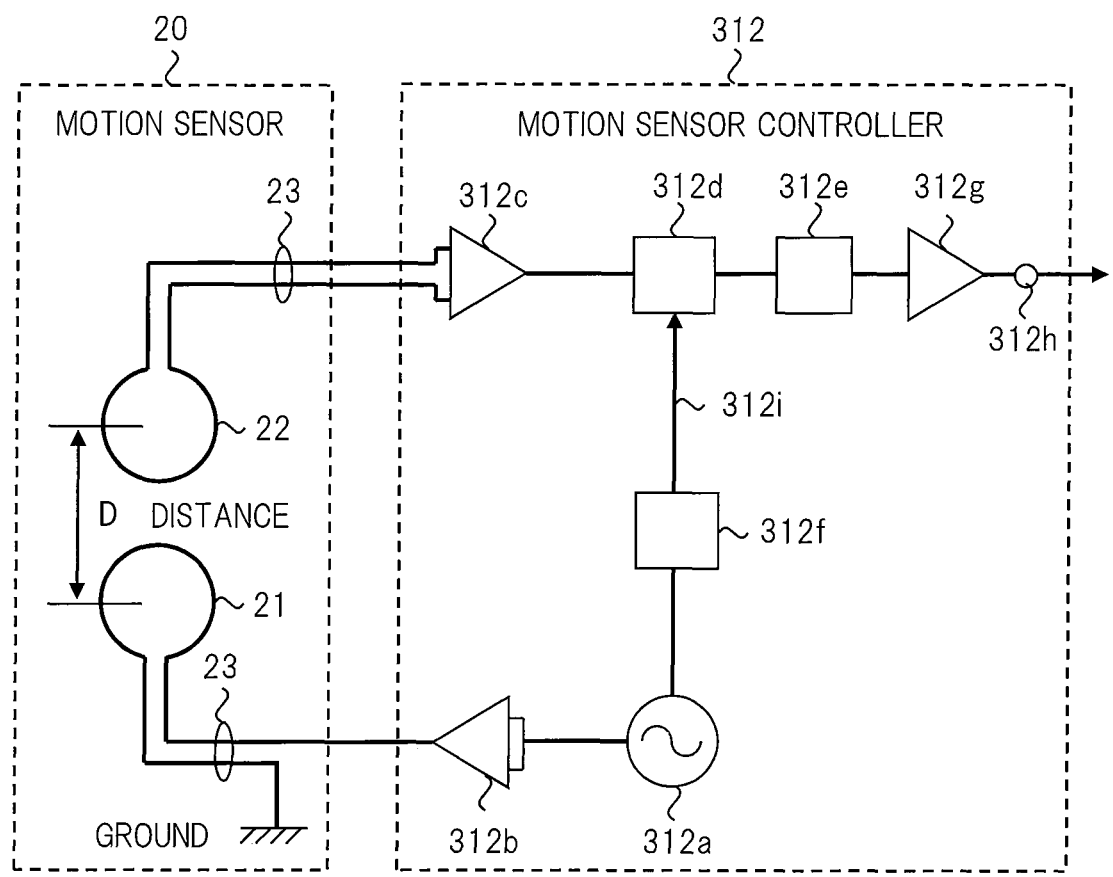
FIG. 6 is a view showing a configuration of a motion sensor controller of the measuring apparatus and the like according to the first embodiment.

FIG. 6 shows a detailed configuration example of the motion sensor controller 312 and the like of the measuring apparatus 3. A distance D between the transmitting coil unit 21 and the receiving coil unit 22 is shown in the motion sensor 20. The motion sensor controller 312 includes an AC generating circuit 312*a*, a current generating amplifier circuit 312*b*, a pre-amplifier circuit 312*c*, a detector circuit 312*d*, an LPF circuit 312*e*, a phase adjusting circuit 312*f*, an amplifier circuit 312*g*, and an output signal terminal 312*h*. The current generating amplifier circuit 312*b* and the phase adjusting circuit 312*f* are connected to the AC generating circuit 312*a*. The transmitting coil unit 21 is connected to the current generating amplifier circuit 312*b* through the signal line 23. The receiving coil unit 22 is connected to the pre-amplifier circuit 312*c* through the signal line 23. The detector circuit 312*d*, the LPF circuit 312*e*, the amplifier circuit 312*g*, and the output signal terminal 312*h* are in turn connected at a post stage of the pre-amplifier circuit 312*c*. The detector circuit 312*d* is connected to the phase adjusting circuit 312*f*.

The AC generating circuit 312*a* generates an AC voltage signal with predetermined frequency. The current generating amplifier circuit 312*b* converts the AC voltage signal into an AC current with predetermined frequency to output the AC current to the transmitting coil unit 21. The transmitting coil unit 21 generates a magnetic field by means of the AC current. The magnetic field causes the receiving coil unit 22 to generate induced electromotive force. The receiving coil unit 22 outputs an AC current generated by the induced electromotive force. The AC current has the same frequency as the predetermined frequency of the AC voltage signal generated by the AC generating circuit 312a.

The pre-amplifier circuit 312c amplifies the detected AC current. The detector circuit 312d detects a signal after amplification on the basis of a reference signal 312i from the phase adjusting circuit 312f. The phase adjusting circuit 312f adjusts a phase of the AC voltage signal with predetermined frequency or twice frequency from the AC generating circuit 312a to output the signal as the reference signal 312i. The LPF circuit 312e limits a band of a signal after detection and outputs the signal. The amplifier circuit 312g amplifies the signal to predetermined voltage. Then, an output signal corresponding to the measured waveform signal is outputted from the output signal terminal 312h.

The waveform signal that is the output signal becomes a signal with a voltage value that indicates the distance D between the two fingers. The distance D and the voltage value can be converted therebetween on the basis of a predetermined calculation formula. The calculation formula can be obtained by calibration. In the calibration, for example, the voltage value is measured in a state where the user has a block having a predetermined length with two fingers of a target hand. A predetermined calculation formula can be obtained from a data set of the voltage value and a distance value in the measured value as an approximate curve that minimizes an error. Further, a size of the hand of the user may be grasped by the calibration, and may be used for normalization of the feature amount or the like. In the first embodiment, the magnetic sensor described above is used as the motion sensor 20, and the method of measurement corresponding to the magnetic sensor is utilized. The present invention is not limited to this combination, and other detector and measuring device, such as an acceleration sensor, a strain gauge, or a high-speed camera, can be applied thereto.

[Processing Flow]

Figure 7:
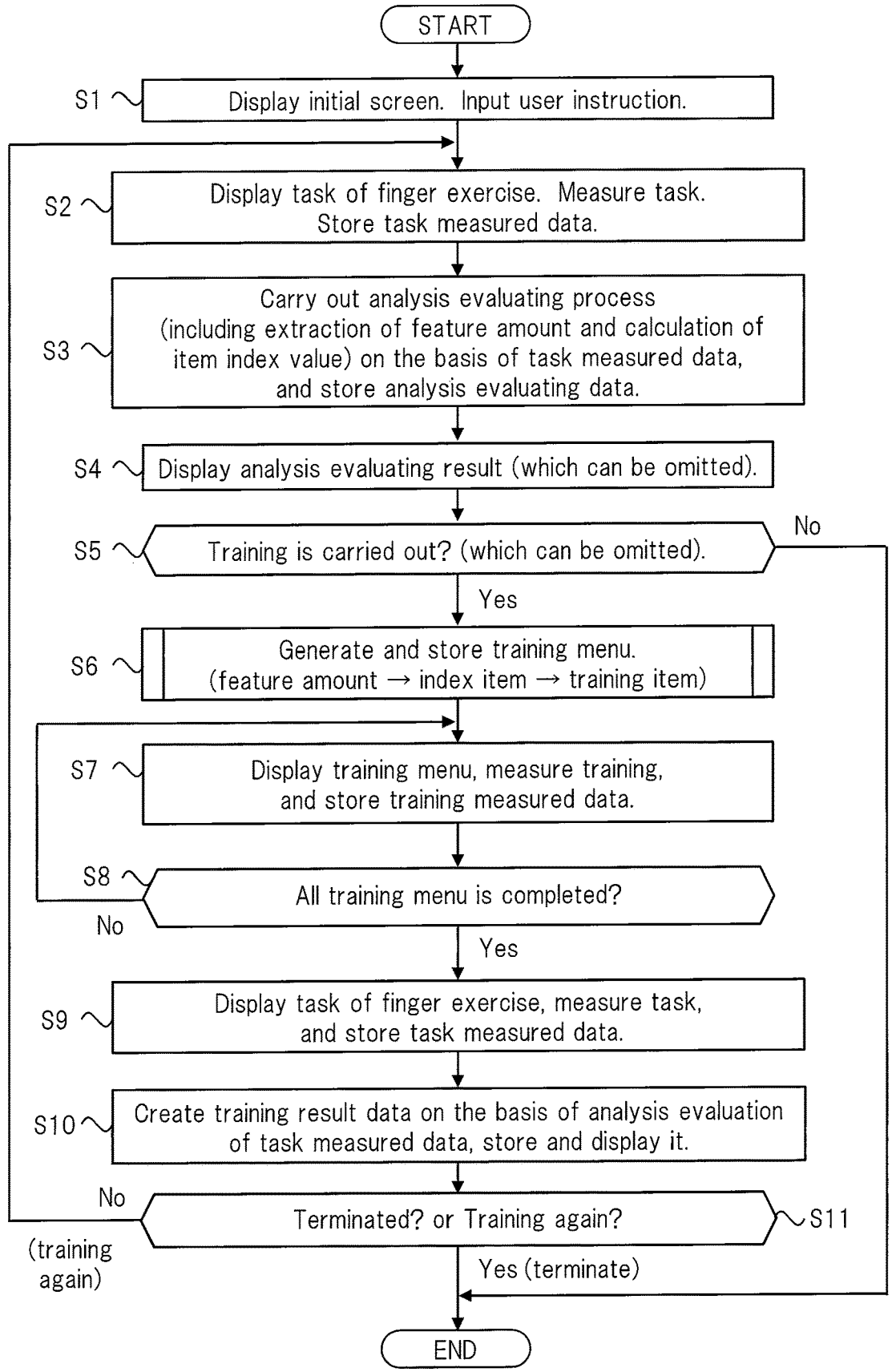
FIG. 7 is a view showing a processing flow of the finger exercise training menu generating system according to the first embodiment.

FIG. 7 shows a processing flow of the whole process that is mainly carried out by the generating apparatus 1 in the finger exercise training menu generating system according to the first embodiment. FIG. 7 includes Steps S1 to S11. Hereinafter, explanation will be made in the order of the Steps.

(S1) A user operates the training apparatus 2. The terminal device 4 displays an initial screen on a display screen. The user selects a desired operation item on the initial screen. For example, an operation item for carrying out training of a finger exercise is selected. The terminal device 4 transmits instruction input information corresponding to the selection to the generating apparatus 1. Further, the user can input user information such as sex and age on the initial screen to register the user information. In that case, the terminal device 4 transmits the inputted user information to the generating apparatus 1. The user information manager 11 of the generating apparatus 1 registers the user information in the user information 41.

(S2) The task processor 12 of the generating apparatus 1 transmits task data for the user to the terminal device 4 on the basis of the instruction input information and the task data 42A of Step S1. The task data contain information on one or more kinds of task regarding the finger exercise. The terminal device 4 displays task information on the finger exercise on the display screen on the basis of the received task data. The user carries out the task for the finger exercise in accordance with the task information displayed on the display screen. The measuring apparatus 3 measures the task, and transmits a measurement result to the generating apparatus 1 as the task measured data. The generating apparatus 1 stores the task measured data in task measured data 42B.

(S3) The analysis evaluating unit 13 of the generating apparatus 1 carries out an analysis evaluating process such as an exercise function of the user on the basis of the task measured data 42B at Step S2, creates analysis evaluating data 43 of the user, and stores the creased analysis evaluating data 43 in the DB 40. In the analysis evaluating process, the analysis evaluating unit 13 extracts a feature amount on the basis of a waveform signal of the task measured data 42B of the user. As the feature amount, there are a distance, speed and the like (which will be described later). The analysis evaluating unit 13 calculates an evaluation value of an index item, which indicates an exercise function and the like, on the basis of the feature amount. As the index item, there are an amount of exercise, endurance and the like (which will be described later). For example, the analysis evaluating unit 13 calculates an evaluation value by predetermined calculation to synthesize the feature amounts associated with the index item for every index item. This calculating method is not limited.

As a simple evaluation method, a predetermined feature amount may be used as the evaluation value as it is. Further, the analysis evaluating unit 13 may correct the extracted feature amount on the basis of an attribute value of the user such as age. Then, a feature amount after correction may be used for evaluation.

(S4) The result outputting unit 16 of the generating apparatus 1 outputs analysis evaluating result information to the display screen of the terminal device 4 on the basis of the analysis evaluating data 43 stored at Step S3. The user is allowed to confirm the analysis evaluating result information, which indicates a state of its own exercise function and the like, on the display screen. The processing flow may be configured so as to omit Step S4.

(S5) In a case where the user wants to carry out training to improve the exercise function or the like, the user selects the operation item for carrying out training on the display screen of the terminal device 4. The terminal device 4 transmits instruction input information corresponding to the selection to the generating apparatus 1. The processing flow may be configured so as to omit Step S5 and automatically shift to a process related to a training menu. In a case where the training is not carried out at Step S5, the processing flow is terminated.

(S6) The training menu processor 14 of the generating apparatus 1 generates a training menu optimized for each user on the basis of the analysis evaluating data 43 stored at Step S3, and stores the training menu in the DB 40 as training menu data 44. For example, the training menu processor 14 picks up at least one of index items whose evaluation value is low on the basis of the feature amount of the analysis evaluating data 43 and the evaluation values of the index items of the user. The training menu processor 14 creates a training menu including training for a training item associated with the index item. A training item that seems to be effective to improve an index item is set so as to be associated with the index item. The term "optimize" means that training for the optimum finger exercise is generated in accordance with a state of the user such as the exercise function indicated by the analysis evaluating result, and a detailed generating system thereof will be described later.

As detailed parameter values of the training item, there are speed, a cycle, frequency (pace), duration time, and the like. Teaching information in the training menu data 44 also contains the detailed parameter values. The teaching information is information that becomes a basis for training or information for conveying the content of training, which is presented on the display screen to the user. The teaching information may be provided as a teaching waveform. Otherwise, the teaching information may be provided as visual information, auditory information, tactile information or the like.

(S7) The training menu processor 14 of the generating apparatus 1 transmits the training menu data of the user generated at Step S6 to the terminal device 4. The terminal device 4 displays the training menu on the display screen on the basis of the training menu data. The user carries out training for a finger exercise in accordance with the training menu displayed on the display screen. The measuring apparatus 3 measures the training, and transmits the measured training to the generating apparatus 1 as training measured data. The generating apparatus 1 stores the training measured data as training measured data 45A.

(S8) The generating apparatus 1 confirms whether all training of the training menu presented to the user is completed or not. For example, the generating apparatus 1 causes the user to carry out plural kinds of training in the training menu in a predetermined order, and grasps what training has been terminated. In a case where the user terminates one kind of training and proceeds to next training, the processing flow returns to Step S7 and the generating apparatus 1 similarly causes the user to carry out the next training. In a case where it is confirmed that all training is terminated, or in a case where the user inputs an instruction to terminate the training on the way, the processing flow shifts to Step S9.

(S9) The generating apparatus 1 first carries out task measurement by the task processor 12 in the similar manner to that at Step S3 for analysis evaluation for a training result of the user this time. This allows the generating apparatus 1 to obtain the latest task measured data 42B of the user.

(S10) The generating apparatus 1 carries out analysis evaluation for the exercise function of the user by the analysis evaluating unit 13 on the basis of the task measured data 42B obtained at Step S9, creates the training result data 45B on the basis of a result thereof, and stores the created training result data 45B in the DB 40. At that time, the analysis evaluating unit 13 calculates an evaluation value for every index item such as an amount of exercise, for example. The generating apparatus 1 transmits the training result data of the user to the terminal device 4. The terminal device 4 displays training result information on the display screen on the basis of the training result data. The user is allowed to confirm his or her state such as the exercise function on the display screen as the training result this time.

Note that the processing flow may be configured so as to omit Steps S9 and S10 as modification example. In the case of such a configuration, a result based on task measurement and analysis evaluation corresponding to Steps S2 to S4 is first displayed when the user utilizes the service next time to carry out training. At that time, the user is allowed to confirm his or her state such as the exercise function.

(S11) The user selects a desired operation item, such as termination or training again, on the display screen of the terminal device 4. The terminal device 4 transmits instruction input information based on the selection to the generating apparatus 1. In a case where termination is selected, the generating apparatus 1 terminates the processing flow. In a case where training again is selected, the processing flow returns to Step S2, and the generating apparatus 1 similarly repeats the processes.

The user can carry out training at desired date and time. In this case, the latest and optimum training menu is generated and presented on the basis of task measurement and analysis evaluating result of the user at that time. This makes it possible to maintain or improve the exercise function of the user.

[Feature Amount]

Figure 8:
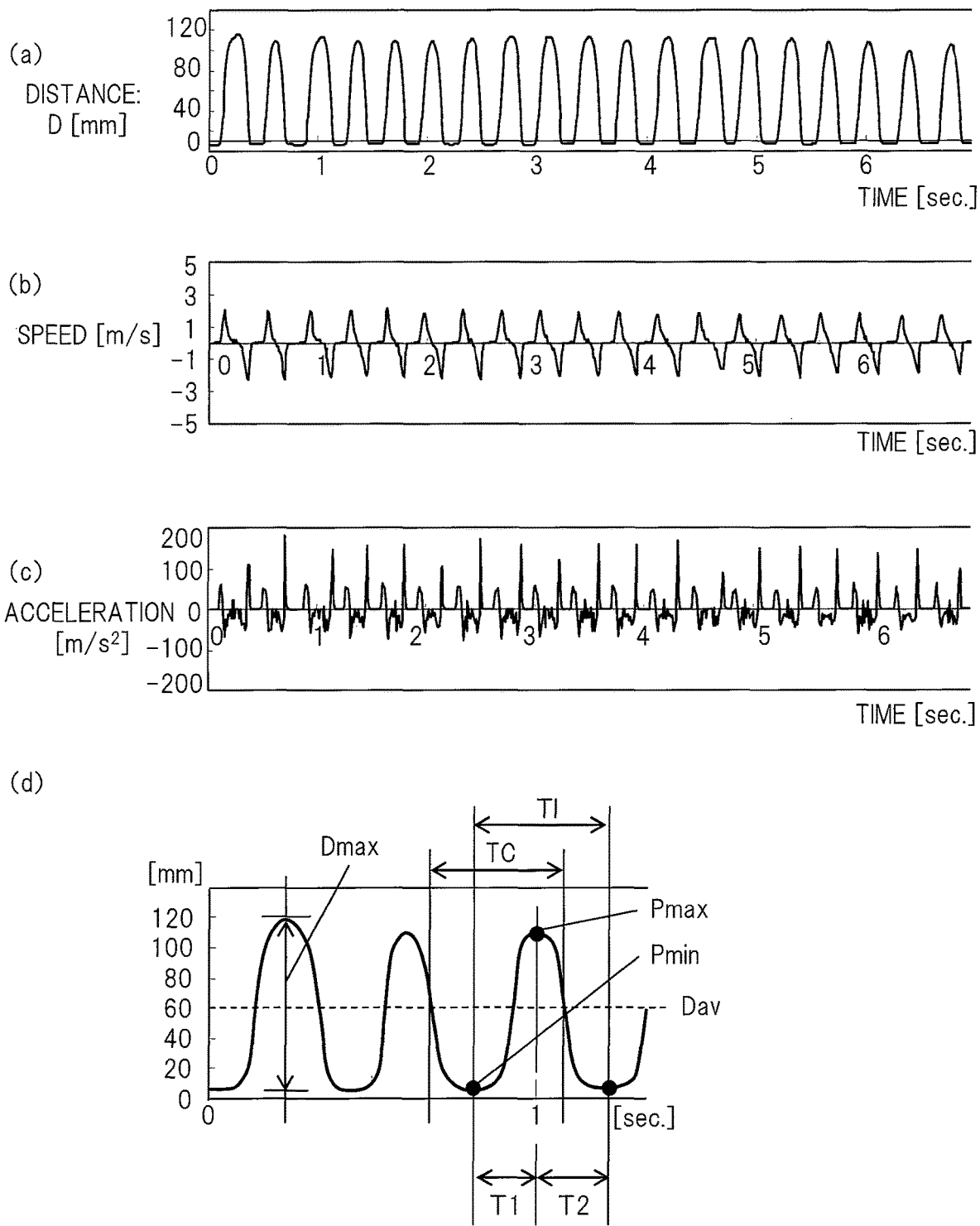
FIG. 8 is a view showing an example of waveform signals of feature amounts according to the first embodiment.

FIG. 8 shows an example of waveform signals of the feature amounts. (a) in FIG. 8 shows a waveform signal of the distance D between two fingers, (b) thereof shows a waveform signal of speed of the two fingers, and (c) thereof shows a waveform signal of acceleration of the two fingers. Speed of (b) is obtained by temporal differentiation of the waveform signal of the distance D of (a). Acceleration of (c) is obtained by temporal differentiation of the waveform signal of the speed of (b). The analysis evaluating unit 13 obtains a waveform signal of a predetermined feature amount like the present embodiment from the waveform signals of the task measured data 42B on the basis of differentiation, integration and the like. Further, the analysis evaluating unit 13 obtains a value by predetermined calculation from the feature amount.

(d) in FIG. 8 shows an example of the feature amount, which is obtained by enlarging (a). (d) shows the maximum value Dmax of the distance D by the finger tap and a tap interval TI. A horizontal broken line indicates an average value Dav of the distance D for all measurement time. The maximum value Dmax indicates the maximum value of the distance D for all measurement time. The tap interval TI is a time corresponding to a cycle TC of a finger tap per one time, and particularly indicates a time from one local minimum point Pmin to next one local minimum point Pmin. Otherwise, (d) indicates the local maximum point Pmax, the local minimum point Pmin, a time T1 for an opening motion and a time T2 for a closing motion in one cycle of the distance D (which will be described later).

Hereinafter, further detailed examples of the feature amount will be described. In the first embodiment, a plurality of feature amounts including the distance, the speed and acceleration as described above and parameter values of the feature amount as described below is used. Note that in the other embodiments, only some feature amounts of the plurality of feature amounts may be used, or the other feature amounts may be used. Details of definition of the feature amounts are not limited.

FIG. 9 shows a portion of a feature amount [distance] of setting information on association of the feature amount with the index item in the administration table 50. This setting of the association is one example, and can be changed. The administration table 50 shown in FIG. 9 has feature amount classification, an identification number, a feature amount parameter, and an index item as a row. The feature amount classification includes [distance], [speed], [acceleration], [tap interval], [phase difference], and [marker tracking]. For example, the feature amount [distance] includes a plurality of feature amount parameters that are respectively identified by identification numbers (1) to (7). A term in parenthesis [ ] of each of the feature amount parameters denotes a unit. Each of the feature amount parameters is associated with a predetermined index item.

The identification number (1) "the maximum amplitude of distance" [mm] is a difference between the maximum value and the minimum value of amplitude in a waveform of the distance ((a) in FIG. 8). A parameter of each of the identification numbers (1), (4), (6), and (7) is associated with an index item F (trackability) and an index item H (amplitude control). The identification number (2) "total moving distance" [mm] is the sum of absolute values of change amounts of the distance in the whole measurement time of one time of measurement. This parameter is associated with an index item A (amount of exercise). The identification number (3) "average of local maximum points of distance" [mm] is an average value of the local maximum points of amplitude in each cycle. This parameter is associated with the index item F (trackability). The identification number (4) "standard deviation of local maximum points of distance" [mm] is a standard deviation regarding the above values.

The identification number (5) "slope (attenuation rate) of approximate curve of local maximum points of distance" [mm/sec.] is a slope of an approximate curve of the local maximum points of amplitude. This parameter mainly indicates an amplitude change during a measurement time due to tiredness. This parameter is associated with an index item B (endurance). The identification number (6) "coefficient of variation of local maximum points of distance" is a coefficient of variation of the local maximum points of amplitude, and a unit thereof is dimensionless quantity (shown by [-]). This parameter is a value obtained by normalizing the standard deviation with the average value. For this reason, an individual difference of a length of each finger can be removed. The identification number (7) "standard deviation of regionally local maximum points of distance" [mm] is a standard deviation of three adjacent local maximum points of amplitude. This parameter is a parameter for evaluating a degree of variation of regional amplitude in a short time.

Hereinafter, each of the feature amount parameters will be described while omitting illustration thereof. The feature amount [speed] includes feature amount parameters indicated by the following identification numbers (8) to (22). The identification number (8) "the maximum amplitude of speed" [m/sec.] is a difference between the maximum value and the minimum value of the speed in the waveform of the speed ((b) in FIG. 8). Each of parameters of the identification numbers (8) to (10) is associated with the index item F. The identification number (9) "average of local maximum points of opening speed" [m/sec.] is an average value regarding the maximum values of speed at the time of an opening motion in the waveform of each finger tap. The opening motion is a motion in which the two fingers make a transition from a closing state to the maximum opening state ((d) in FIG. 8). The identification number (10) "average of local maximum points of closing speed" [m/sec.] is an average value regarding the maximum values of speed at the time of a closing motion. The closing motion is a motion in which two fingers make a transition from the maximum opening state to the closing state. The identification number (11) "standard deviation of local maximum points of opening speed" [m/sec.] is a standard deviation regarding the maximum values of speed at the time of the opening motion described above. The identification number (12) "average of local maximum points of closing speed" [m/sec.] is a standard deviation regarding the maximum value of speed at the time of the closing motion described above. Each of parameters of the identification numbers (11), (12), (15), and (16) is associated with the index item F and the index item H.

The identification number (13) "energy balance" [-] is a ratio of a sum of squares of speed during the opening motion and a sum of squares of speed during the closing motion. Each of parameters of the identification numbers (13) and (17) to (22) is associated with an index item G. The identification number (14) "total energy" [m²/sec.²] is a sum of squares of speed during the whole measurement time. This parameter is associated with the index item A. The identification number (15) "coefficient of variation of local maximum points of opening speed" [-] is a coefficient of variation regarding the maximum value of speed at the time of the opening motion, and is a value obtained by normalizing a standard deviation by an average value. The identification number (16) "average of local maximum points of closing speed" [m/sec.] is a coefficient of variation regarding the minimum values of speed at the time of the closing motion.

The identification number (17) "the number of times of shaking" [-] is a number obtained by subtracting the number of times of large opening/closing finger taps from the number of times of reciprocation in which plus and minus of a waveform of speed are changed. The identification number (18) "average of distance ratios at peak of opening speed" [-] is an average value regarding a ratio with a distance at the time of the maximum value of speed during the opening motion in a case where amplitude of the finger tap is set to 1.0. The identification number (19) "average of distance ratios at peak of closing speed" [-] is an average value regarding the similar ratio with a distance at the time of the minimum value of speed during the closing motion. The identification number (20) "ratio of distance ratio at peak of speed" [-] is a ratio between a value of the identification number (18) and a value of the identification number (19). The identification number (21) "standard deviation of distance ratio at peak of opening speed" [-] is a standard deviation regarding a ratio with a distance at the time of the maximum value of speed during the opening motion in a case where the amplitude of the finger tap is set to 1.0. The identification number (22) "standard deviation of distance ratio at peak of closing speed" [-] is a standard deviation regarding the similar ratio with a distance at the time of the minimum value of speed during the closing motion.

The feature amount [acceleration] includes feature amount parameters indicated by the following identification numbers (23) to (32). The identification number (23) "the maximum amplitude of acceleration" [m/sec.²] is a difference between the maximum value and the minimum value of acceleration in the waveform of acceleration ((c) in FIG. 8). Each of parameters of the identification number (23) to (27) is associated with the index item F. The identification number (24) "average of local maximum points of opening acceleration" [m/sec.²] is an average of local maximum values of acceleration during the opening motion, and is a first value of four kinds of extreme values that appear in one cycle of a finger tap. The identification number (25) "average of local minimum points of opening acceleration" [m/sec.²] is an average of local minimum values of acceleration during the opening motion, and is a second value of the four kinds of extreme value. The identification number (26) "average of local maximum points of closing acceleration" [m/sec.²] is an average of local maximum values of acceleration during the closing motion, and is a third value of the four kinds of extreme value. The identification number (27) "average of local minimum points of closing acceleration" [m/sec.²] is an average of local minimum values of acceleration during the closing motion, and is a fourth value of the four kinds of extreme value.

The identification number (28) "average of contact times" [sec.] is an average value of contact times in the closing state of the two fingers. Each of parameters of the identification numbers (28) to (32) is associated with the index item G. The identification number (29) "standard deviation of contact time" [sec.] is a standard deviation of the contact times described above. The identification number (30) "coefficient of variation of contact time" [-] is a coefficient of variation of the contact time described above. The identification number (31) "the number of zero crossing of acceleration" [-] is the average number of times plus and minus of acceleration are changed in one cycle of the finger tap. This value becomes twice ideally. The identification number (32) "the number of times of freezing" [-] is a value obtained by subtracting the number of times of large opening/closing finger taps from the number of times of reciprocation in which plus and minus of acceleration are changed in one cycle of the finger tap.

The feature amount [tap interval] includes feature amount parameters indicated by the following identification numbers (33) to (41). The identification number (33) "the number of times of taps" [-] is the number of times of finger taps during the whole measurement time of measurement once. Each of parameters of the identification numbers (33) to (35) is associated with the index item A. The identification number (34) "average of tap interval" [sec.] is an average value of the tap intervals described above in the waveform of the distance ((d) in FIG. 8). The identification number (35) "tap frequency" [Hz] is frequency that a spectrum becomes the maximum in a case where the waveform of the distance is subjected to Fourier transform. The identification number (36) "standard deviation of tap interval" [sec.] is a standard deviation regarding the tap intervals. Each of parameters of the identification numbers (36) to (40) is associated with an index item C and an index item I.

The identification number (37) "tap interval coefficient of variation" [-] is a coefficient of variation regarding the tap intervals, and is a value obtained by normalizing a standard deviation by an average value. The identification number (38) "variation in tap interval" [mm$^2$] is an integrated value when frequency is in a range from 0.2 to 2.0 Hz in a case where the tap interval is subjected to spectral analysis. The identification number (39) "degree of distortion of tap interval distribution" [-] is a degree of distortion in frequency distribution of the tap interval, and indicates a degree that the frequency distribution is distorted compared with normal distribution. The identification number (40) "standard deviation of regional tap interval" [sec.] is a standard deviation regarding three adjacent tap intervals. The identification number (41) "slope (attenuation rate) of approximate curve of tap interval" [-] is a slope of a curve obtained by approximating the tap interval. This slope indicates a change in the tap interval mainly due to tiredness during the measurement time. This parameter is associated with the index item B.

The feature amount [phase difference] includes feature amount parameters indicated by the following identification numbers (42) to (45). The identification number (42) "average of phase differences" [°] is an average value of phase differences in the waveforms of both hands. The phase difference is an index value that indicates a gap of a finger tap by a left hand with respect to a right hand as an angle in a case where one cycle of the finger tap by the right hand is defined as 360°. In a case where there is no gap, the phase difference is set to 0°. The larger the value of the identification number (42) or (43) is, the larger the gap between both hands is. This indicates to be instability. Each of parameters of the identification numbers (42) to (45) is associated with the index item D and an index item J. The identification number (43) "standard deviation of phase difference" [°] is a standard deviation regarding the phase difference described above. The identification number (44) "degree of similarity of both hands" [-] is a value indicating correlation when time deviation is zero in a case where a mutual correlation function is applied to the waveforms of the left hand and the right hand. The identification number (45) "time deviation when degree of similarity of both hands becomes the maximum" [sec.] is a value indicating the time deviation when the correlation of the identification number (44) becomes the maximum.

The feature amount [marker tracking] includes feature amount parameters indicated by the following identification numbers (46) to (47). The identification number (46) "average of delay times from marker" [sec.] is an average value regarding a delay time of a finger tap with respect to a time indicated by a periodical marker. The marker corresponds to stimulation such as visual stimulation, auditory stimulation, or tactile stimulation. This parameter value is based on a point of time in the closing state of the two fingers. Each of parameters of the identification numbers (46) and (47) is associated with an index item E. The identification number (47) "standard deviation of delay time from marker" [sec.] is a standard deviation regarding the delay times described above.

[Index Item]

FIG. 10 shows a configuration example of association between the index item and the training item in the administration table 50. The administration table 50 shown in FIG. 10 includes an index item ID, an index item, and a training item as a row. The index item ID indicates an identifier of the index item, and is indicated by any of A to J or the like in the present embodiment. The index item corresponds to an exercise function item that becomes target training. The training item is an item for making up a training menu. One or more training item is associated with and set to one index item. This setting for association is one example, and can be changed.

In the present embodiment, the index item includes (A) "amount of exercise", (B) "endurance", (C) "rhythmicity (rhythm generating force)", (D) "cooperativeness of both sides", (E) "marker trackability", (F) "magnitude of exercise", (G) "waveform balance", (H) "amplitude control", (I) "speed control", and (J) "independent control of both hands".

In the present embodiment, training items #1 to #10 respectively associated with the index items A to J are shown as the training item. The training item #1 is training for improving the amount of exercise, and is a finger tap with speed faster than speed at the time of past training of the finger tap by the user. The faster the speed is, the higher a difficulty level thereof is. The speed and a pace are also expressed by a cycle or frequency ([Hz]). For example, in a case where a pace during previous training was 1 Hz, a pace during this training is set to 2 Hz.

The training item #2 is training for improving endurance, and is a finger tap for a duration time longer than a duration time at the time of past training of the finger tap by the user. The longer the duration time is, the higher a difficulty level thereof is. For example, in a case where a duration time during previous training was 30 seconds, a duration time during this training is set to 40 seconds.

The training item #3 is training for improving rhythmicity, and is an accurate finger tap with a pace slower than a pace at the time of past training of the finger tap by the user or a predetermined pace. The predetermined pace is an average pace of healthy persons in a case where the user is a patient, for example. The term "accurate finger tap" means that deviation of a point of time of the finger tap with respect to each point of time in accordance with the pace is small. The slower the pace is, the higher a difficulty level thereof is. In addition, the smaller time deviation to be permitted is, the higher the difficulty level thereof becomes.

The training item #4 is training for improving cooperativeness of both sides, and is a finger tap for accurately both hands at the same time or alternately with a pace slower than a pace at the time of past training of the finger tap by the user or a predetermined pace. The term "accurately both hands at the same time or alternately" means that deviation of a point of time of the finger tap by both hands or one hand of the right and left hands with respect to each point of time in accordance with the pace is small. The slower the pace is, the higher a difficulty level thereof becomes. In addition, the smaller time deviation to be permitted is, the higher the difficulty level thereof becomes.

The training item #5 is training for improving marker trackability, and is a finger tap to be accurately matched to a position of a marker with a pace faster than a pace at the time of past training of the finger tap by the user or a predetermined pace. The marker is controlled so as to switch between a display state and a non-display state thereof or change a display position thereof in the display screen, for example. The user causes his or her finger to track the marker in accordance with the display position thereof, and carries out the finger tap. The faster the pace of switching the marker is and the smaller a positional gap to be permitted with respect to the marker is, the higher the difficulty level thereof becomes.

The training item #6 is training for improving the magnitude of exercise, and is a finger tap with opening/closing amplitude larger than opening/closing amplitude at the time of past training of the finger tap by the user or predetermined opening/closing amplitude. The opening/closing amplitude is a difference between a distance at the time of the opening state and a distance at the time of the closing state while opening and closing two fingers. In a case where the user is a patient, predetermined opening/closing amplitude is an average opening/closing distance of healthy persons, for example. The larger the opening/closing amplitude is, the higher the difficulty level thereof becomes.

The training item #7 is training for improving a waveform balance, and is a finger tap to be matched to a teaching waveform of the display screen with a pace slower than that at the time of past training of the finger tap by the user or a predetermined pace and opening/closing amplitude larger than that at the time of past training of the finger tap by the user or predetermined opening/closing amplitude. In this training, the teaching waveform for teaching the pace, the opening/closing amplitude, and the like to the user, for example, a sine wave is displayed on the display screen of the terminal device 4. The user carries out a finger tap so as to match with the teaching waveform. The smaller a gap to be permitted with respect to the teaching waveform is, the higher the difficulty level thereof becomes.

The training item #8 is training for improving amplitude control; two or more kinds of opening/closing amplitude are contained during one training; and the training item #8 is a finger tap while changing the opening/closing amplitude. For example, in the teaching waveform, a sine wave with first opening/closing amplitude of 50 mm and a sine wave with second opening/closing amplitude of 100 mm are alternately repeated every one cycle and are displayed. The more the plural kinds of opening/closing amplitude exist and the more frequent the change thereof is, the higher the difficulty level thereof becomes.

The training item #9 is training for improving speed control; two or more kinds of speed are contained during one training; and the training item #9 is a finger tap while changing the speed. For example, in the teaching waveform, a sine wave with 1 Hz corresponding to first speed and a sine wave with 2 Hz corresponding to second speed are alternately repeated every one cycle and are displayed. The more the plural kinds of speed exist and the more frequent the change thereof is, the higher the difficulty level thereof becomes.

The training item #10 is training for improving independent control of both hands, and is a finger tap with different cycles or the like with respect to the right and left hands by using both hands. For example, there are various kinds of combinations such as a combination of a cycle of the left hand with 1 Hz and a cycle of the right hand with 2 Hz, or a combination of a cycle of the left hand with 2 Hz and a cycle of the right hand with 3 Hz. Further, for example, in the teaching waveform, a predetermined phase difference is set at timing of finger taps by the left hand and the right hand, and the teaching waveform is displayed. The predetermined phase difference is 90°, for example, except for both hands at the same time (in which the phase difference is 0°) or alternately (in which the phase difference is 180°).

[Training Menu Generating Process (1)]

Details of the training menu generating process areas follows. The training menu processor 14 selects training items to make up a training menu on the basis of a feature amount of an analysis evaluating result and an evaluation value of an index item of a task. The training menu processor 14 generates a combination of training items from the selected training items, and further adjusts a detailed parameter value of each of the training items to make up the training menu.

For example, the identification number (2) "total moving distance" in the feature amount [distance], the identification number (14) "total energy" in the feature amount [speed], the identification number (33) "the number of times of taps" in the feature amount [tap interval] and the like are associated with the index item A (amount of exercise). For example, in a case where a value of each of feature amount parameters related to the index item A or the evaluation value obtained by calculating the sum of the values of the feature amount parameters is a low value in the context of a predetermined condition, the training menu processor 14 picks up the index item A. As the predetermined condition, a threshold value set in advance may be used. Further, as the predetermined condition, it may be determined whether the value or the evaluation value is relatively low value in analysis evaluating data of the user or not without using the threshold value or the like. The same applies to the other index items.

The training menu processor 14 selects a training item associated with the picked-up selected index item, for example, the index item A. The training item is an item that defines training for improving an amount of exercise of the index item A. Further, at that time, in a case where there is a plurality of training items associated with the selected index item, the training menu processor 14 may select one or more training item from the plurality of training items. For example, the training menu processor 14 selects the training item #1 of the training items associated with the index item A in the administration table 50.

The training menu processor 14 makes up a training menu by using the selected one or more training item. In a case where a plurality of training items is selected, the training menu processor 14 makes up a training menu by means of a combination of the plurality of training items.

[Training Menu Generating Process (2)]

In the training menu generating process, a first system configured to generate the optimum training menu to each individual user is as follows. The training menu processor 14 picks up one or more of index items corresponding to lower parameter values of feature amounts compared with a predetermined standard or index items whose evaluation value is low on the basis of the analysis evaluating data 43 of the user. Note that the evaluation values of the plurality of index items are normalized so that they can be compared. This normalization is carried out by using an average of the indices and a standard deviation thereof in a healthy person DB. In other words, it can be realized by subtracting the average and dividing it by the standard deviation. The generating apparatus 1 appropriately refers to information from the healthy person DB that is held inside or outside the generating apparatus 1. Evaluation values of the index items A to E are −0.6, 0.6, −0.8, −0.4, and 0.9, respectively. In a case where the index items are arranged in ascending order of the evaluation values, they are arranged as the index items C, A, D, B, and E in this order. The training menu processor 14 selects a predetermined number of index items whose evaluation values are lower from the index items. At this time, they may be determined by using a threshold value, or the user may select a prescribed number set in advance. For example, in the case of selecting them by using the threshold value, the index items C, A, and D are selected as three index items whose evaluation values are equal to or less than the threshold value. The training menu processor 14 selects a predetermined number of training items from training items associated with each of the index items C, A, and D. For example, in a case where one training item is to be selected for each index item, the training items #3, #1, and #4 are selected. The training menu processor 14 makes up a training menu by using the training items #3, #1, and #4.

In the first system, the order or sequence is not defined for the plurality of index items and plural kinds of training in the training menu. The generated training menu includes three kinds of training containing first training by the training item #3, second training by the training item #1, and third training the training item #4, for example. The user is allowed to select desired training from the plural kinds of training presented in the training menu and carry out the selected training.

A second system is as follows. In the second system, the order or sequence is defined for a plurality of index items and plural kinds of training in a training menu. The second system uses a known partially learning method. The partially learning method is a method in which an exercise is divided into a plurality of elements, and exercise learning proceeds so as to improve the respective elements in turn. The training menu processor 14 picks up and selects a plurality of index items on the basis of the analysis evaluating data 43 of the user in the similar manner to that of the first system. The training menu processor 14 selects a plurality of training items associated with the plurality of index items thus selected. For example, in the context of a predetermined condition, the case where a value of (36) "standard deviation of tap interval" is the worst, a value of (2) "total moving distance" is the second worst, and a value of (42) "average of phase differences" is the third worse is as follows. The identification number (36) described above is associated with the index item C (rhythmicity), the identification number (2) described above is associated with the index item A (amount of exercise), and the identification number (42) described above is associated with the index item D (cooperativeness of both sides). Herewith, the index items C, A, and D are selected in this order.

The training menu processor 14 makes up a training menu for preferentially improving the index items C, A, and D in this order. The training menu processor 14 similarly selects training items associated with the selected index items C, A, and D, for example, the training items #3, #1, and #4. The training menu processor 14 generates a combination of the training items by means of permutation and combination from the selected training items #3, #1, and #4. The combination of the training items includes a single training item, a set of two training items, a set of three training items, and the like.

For example, the training menu processor 14 generates a training menu that includes three kinds of training of first training by the index item C, second training by the index item A, and the third training by the index item D in this order. The training menu processor 14 generates a training menu that includes five kinds of training of fourth training by a set of the index item C and the index item A and fifth training by a set of the index item C, the index item A and the index item D following the three kinds of training described above in this order. The training menu processor 14 may adopt a part of a combination in accordance with a degree of priority without limiting the combination of all kinds of training, or may adjust the order thereof.

[Training Menu Generating Process (3)]

Further, in a case where it is determined that training of each training item in a training menu once is insufficient, the controller 101 may generate the training menu so as to cause the user to carry out the same training item in the training menu several times. For example, the controller 101 may generate a training menu including an instruction to repeat first training by the index item C the predetermined number of times. Further, the controller 101 may set a target value for every training corresponding to each training item in the training menu, and determine whether a training result reaches the target value or not, a degree of achievement thereof, and the like. The target value may be the same as a detailed parameter value such as a cycle of the training item, or may be different therefrom. The controller 101 may control to cause the user to carry out training of the same training item in accordance with the determination until the training result reaches the target value.

[Training Menu Generating Process (4)]

The training menu processor 14 may determine a pace or a duration time, which is the detailed parameter value of the training described above, in accordance with the attribute value in the user information 41, the analysis evaluating result, a result from past training of the user, and the like. An example to constitute training based on an attribute value of an individual user is as follows. For example, the training menu processor 14 may select a training item or a detailed parameter value in accordance with age of the user so as to refrain from or reduce an exercise related to the index item of endurance. Further, the training menu processor 14 may select a method of providing the teaching information in accordance with eyesight or hearing of the user, for example. For example, the training menu processor 14 does not provide training using visual stimulation to a user with low eyesight, but provides training using auditory stimulation to such a user. Further, for example, the training menu processor 14 may select training based on disease and a symptom thereof of the user, a severity score and the like or a detailed parameter value thereof. For example, in the case of dementia, the training menu processor 14 provides training by which improvement of dementia is expected. Further, for example, the training menu processor 14 may provide training based on a dominant hand of the user. For example, in a case where the dominant hand of the user is a right hand, the training menu processor 14 may provide training for improving the right hand, or provide training for improving a left hand conversely. Further, the training menu processor 14 may provide training in which a balance of a load or the like between a right hand and a left hand is adjusted.

[Training Menu Generating Process (5)]

The training menu processor 14 may generate a training menu including training in which an exercise load is qualitatively applied to the user. For example, by combining a plurality of training items and/or a plurality of detailed parameter values, this training is training in which the user is caused to carry out qualitatively different exercises during one training by temporally switching the exercises. For example, an exercise of one-hand free run is basically an exercise to cause the user to carry out finger tapping by opening/closing of two fingers as large amplitude as possible and as quickly as possible. For example, the training menu processor 14 sets amplitude that is the detailed parameter value by combining two kinds of amplitude. For example, in a case where first amplitude is 10 cm and second amplitude is 3 cm, the training menu processor 14 generates training to alternately switch the two kinds of amplitude every finger tap and repeat it.

Further, the training menu processor 14 may provide training to cause the user to carry out a qualitatively different exercise by right and left hands at the same time. For example, the training menu processor 14 may provide training for finger taps of the left hand at a pace with 2 Hz and the right hand at a pace with 3 Hz. Further, for example, the training menu processor 14 may construct training using a finger exercise other than the finger tapping. For example, there is an exercise to cause the user to open and close five fingers of a hand as a whole. Further, the exercise may be an exercise to move parts of a body of the user other than the fingers such as foot or leg together with the finger exercise. For example, the exercise may be an exercise to move a right foot at the same time as a finger tap of a left hand.

[Training Menu Generating Process (6)]

The finger tapping described above is a cooperative exercise by two fingers, that is, an exercise to move both of the two fingers. The exercise is not limited to this, and it is possible to generate finger tapping to move only one finger as the other kinds of finger tapping. For example, a thumb that is one finger of the two fingers becomes a basis to fix a position, and a forefinger that is another finger, for example, is moved to open and close therebetween. In this case, it is also possible to generate the training menu similarly. Further, the training menu processor 14 may generate a training menu obtained by combining finger tapping to move two fingers and finger tapping to move one finger. In the case of a second embodiment (will be described later), a fixed point for fixedly arranging the one finger can be displayed on a display screen of a touch panel.

[Display Screen (1)—Menu]

Figure 11:
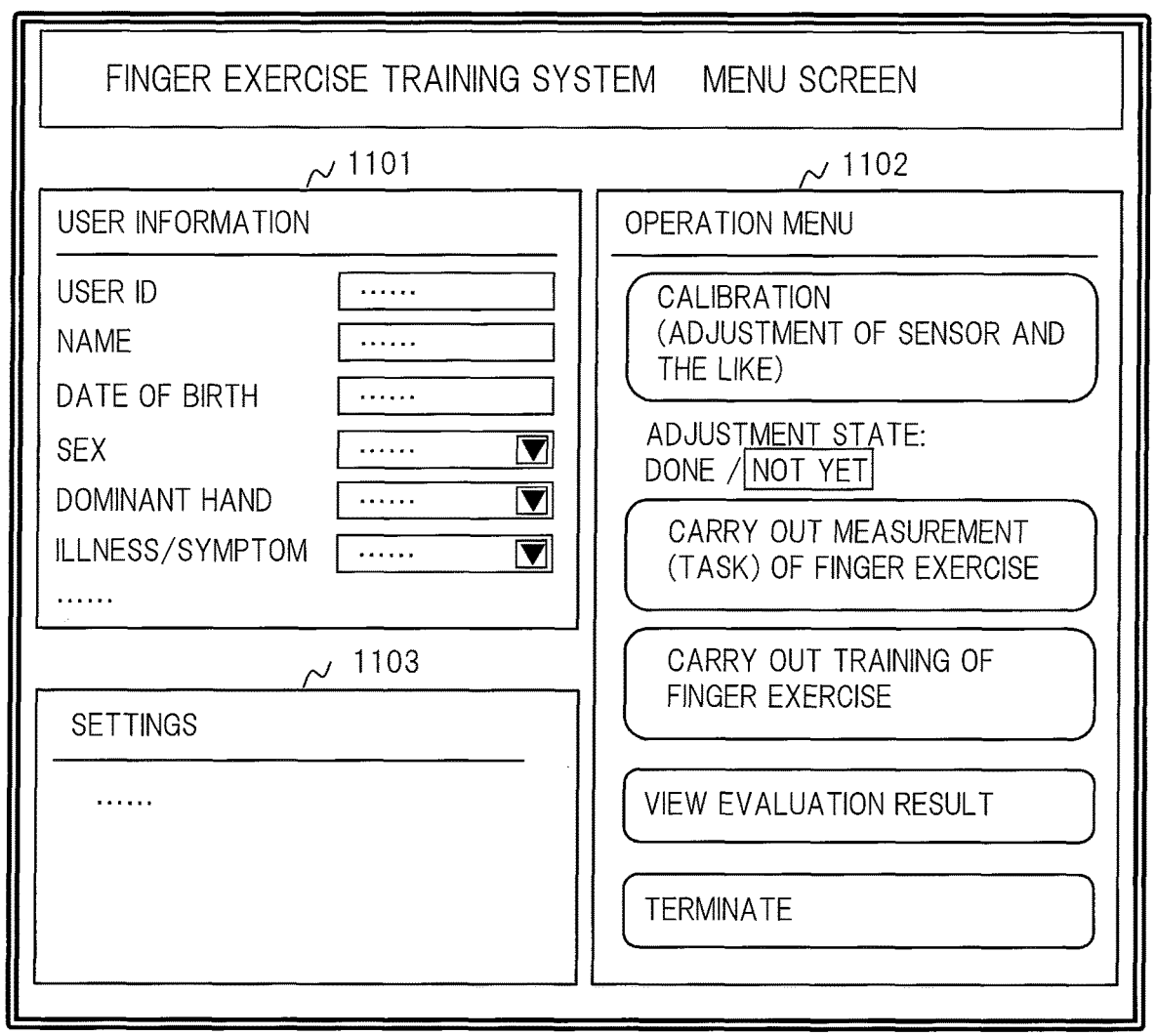
FIG. 11 is a view showing a menu screen as an example of a display screen according to the first embodiment.

FIG. 11 shows an example of a menu screen that is an initial screen for service as an example of the display screen of the terminal device 4. A user information column 1101, an operation menu column 1102, a setting column 1103, and the like are included in this menu screen.

The user is allowed to input and register user information via the user information column 1101. In a case where user information that has already been inputted into an electronic health record or the like exists, the present system may be linked to the user information. As examples of inputtable user information, there are a user ID, a name, date of birth or age, sex, a dominant hand, disease and a symptom thereof (disease/symptom), memo and the like. The dominant hand can be selected and inputted from a right hand, a left hand, both hands, and unknown. The disease/symptom may be selected and inputted from options in a list box, for example, or can be inputted by an arbitrary text. In a case where the present system is utilized in a hospital or the like, a doctor or the like may input the user information in place of the user.

The present finger exercise training menu generating system can be applied to the case where user information is not registered. In such a case, it is impossible or hard to generate a suitable training menu based on an attribute value of the user, but it is possible to generate a training menu based on a task measuring result and the like this makes it possible to obtain an appropriate effect.

Operation items for function provided by the service are displayed in the operation menu column 1102. The operation items include "calibration", "carry out measurement (or a task) of a finger exercise", "carry out training for a finger exercise", "view an evaluation result", "terminate" and the like. In a case where the operation item "calibration" is selected, the calibration described above, that is, a process related to adjustment of the motion sensor 20 with respect to fingers of the user is carried out. A state of whether it has already been adjusted or not is displayed. In a case where the operation item "carry out measurement (or a task) of a finger exercise" is selected, the display screen shifts to a task measuring screen for analyzing a state such as an exercise function of the user. In a case where the operation item "carry out training for a finger exercise" is selected, the task measurement is omitted and the display screen shifts to a training screen. In a case where the operation item "view an evaluation result" is selected, the display screen shifts to an evaluation result screen when any analysis evaluating result exists already. In a case where the operation item "terminate" is selected, the present service is terminated.

User setting can be carried out in the setting column 1103. For example, in a case where there is a type of training that the user want to carry out particularly, the user is allowed to select and set the exercise from options. In a case where there is this setting, the generating apparatus 1 generates a training menu by preferentially using a training item corresponding to the type of exercise specified by the user.

[Display Screen (2)—Task Measurement]

Figure 12:
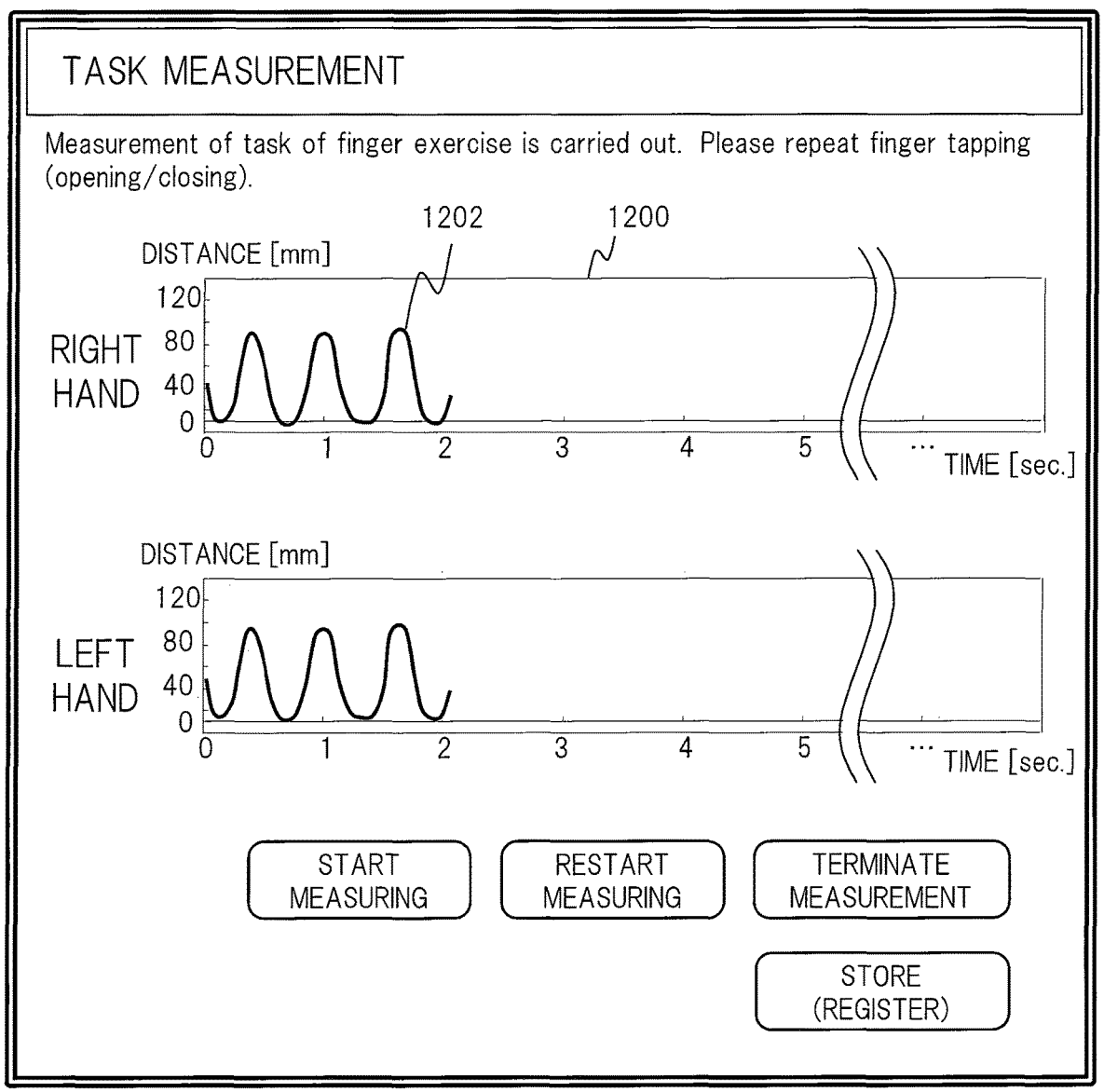
FIG. 12 is a view showing a task measuring screen as an example of the display screen according to the first embodiment.

FIG. 12 shows a task measuring screen as another example. Task information is displayed on this screen. For example, a graph 1200 in which a horizontal axis denotes a time and a vertical axis denotes a distance between two fingers with respect to each of right and left hands is displayed. Other teaching information for explaining task content may be outputted on the screen. For example, an area for video that explains the task content via video and audio may be provided. Operation buttons such as "start measuring", "restart measuring", "terminate measurement", or "store (or register)" are provided in the screen, and the user can select any of the operation buttons. The user selects the operation button "start measuring" in accordance with task information of the screen, and carries out an exercise for a task. The measuring apparatus 3 measures the exercise for the task to obtain a waveform signal. The terminal device 4 displays a measured waveform 1202 corresponding to the waveform signal during measurement on the graph 1200 in real time. The user selects the operation button "terminate measurement" after the exercise. In a case where the measurement is established, the user selects the operation button "store (or register)". The measuring apparatus 3 transmits task measured data to the generating apparatus 1.

[Display Screen (3)—Evaluation Result]

Figure 13:
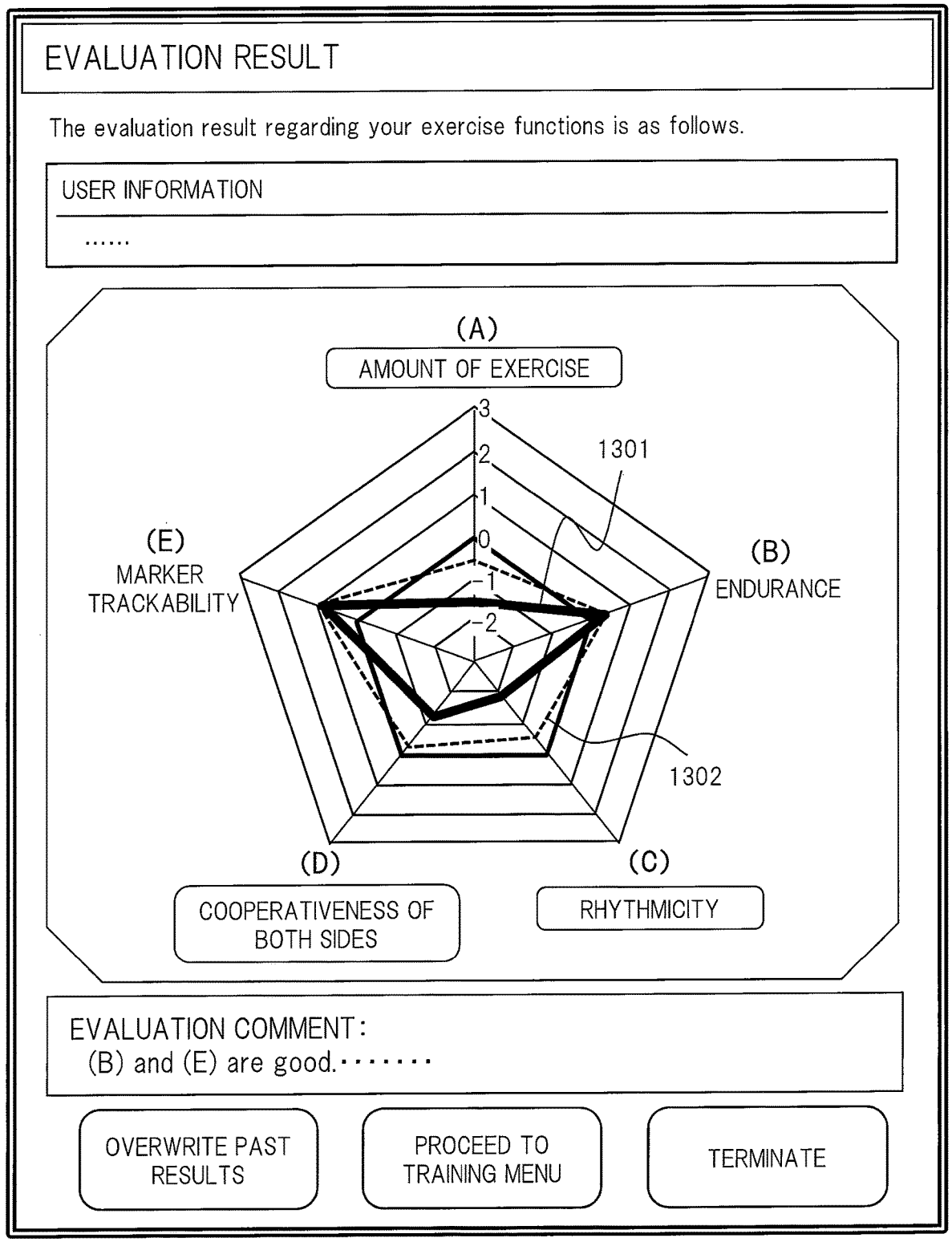
FIG. 13 is a view showing an evaluation result screen as an example of the display screen according to the first embodiment.

FIG. 13 shows an evaluation result screen as still another example. Analysis evaluating result information on the task is displayed on this screen. The present screen is automatically displayed after analysis evaluation of the task. In the present embodiment, the case where evaluation values of five index items, that is, the index items A to E are displayed as a graph in a radar chart form. A solid frame line 1301 denotes an analysis evaluating result after task measurement but before training this time. A broken frame line 1302 denotes an analysis evaluating result after the training this time (which will be described later). The present embodiment is not limited to a method of displaying feature amounts and evaluation values thereof in the radar chart form, and a method of displaying a graph or the like in a predetermined form may be adopted. The evaluation value may be converted and displayed in a record score form (for example, on a scale of 1 to 100) or the like. An evaluation comment regarding the analysis evaluating result or the like may be displayed in addition to the graph of the evaluation values. The analysis evaluating unit 13 creates the evaluation comment. For example, a message such as "(B) and (E) are good." is displayed. Operation buttons such as "overwrite a past result", "proceed to a training menu", or "terminate" are provided in the screen. In a case where the operation button "proceed to a training menu" is selected, the generating apparatus 1 causes the terminal device 4 to shift to a training menu screen. In a case where the operation button "terminate" is selected, the generating apparatus 1 causes the terminal device 4 to shift to the initial screen.

[Display Screen (4)—Training Menu]

Figure 14:
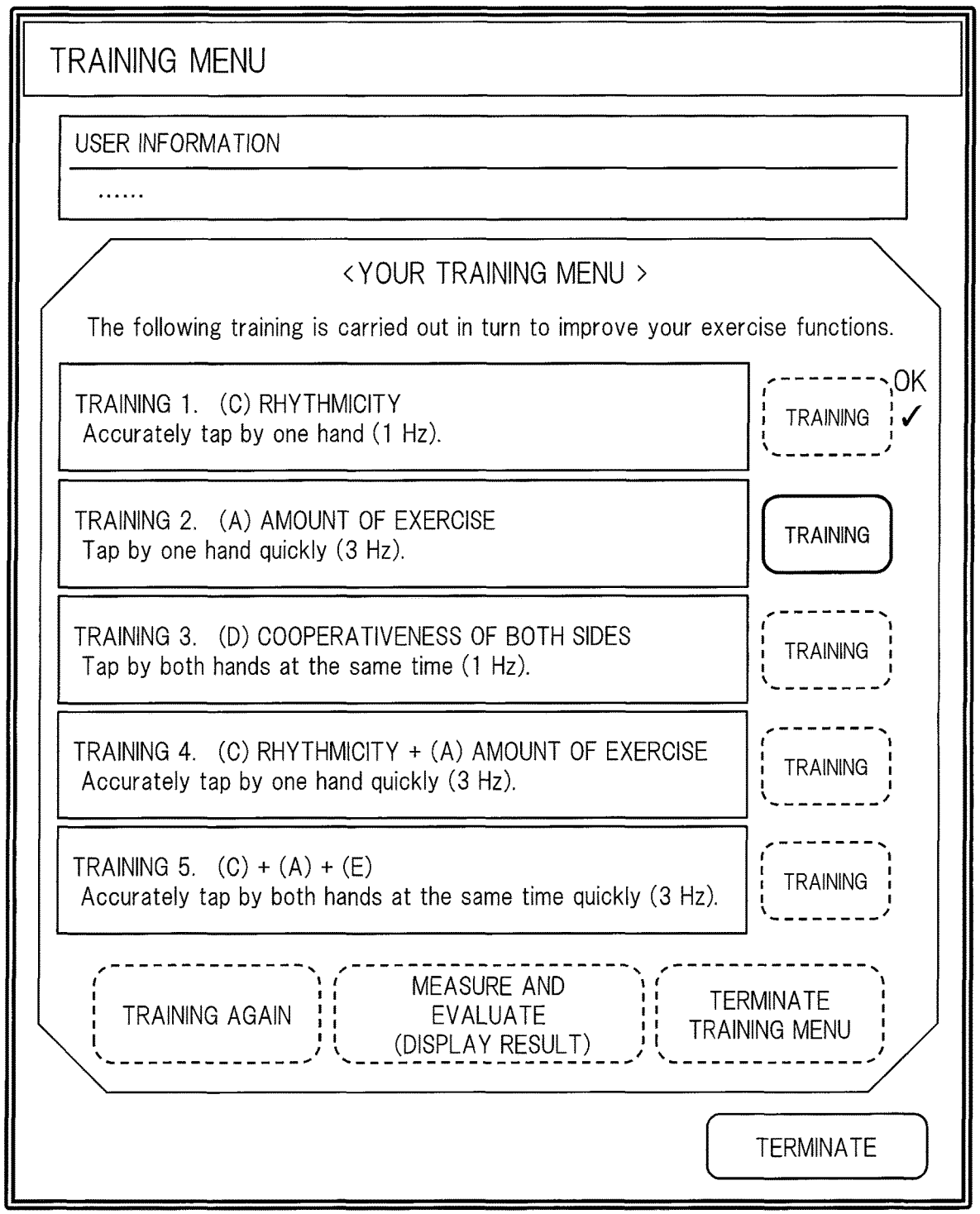
FIG. 14 is a view showing a training menu screen as an example of the display screen according to the first embodiment.

FIG. 14 shows a training menu screen as still another example. A training menu for the user is displayed on this screen. In the present embodiment, the training menu generated this time by the second system described above includes five kinds of training from first training "training 1" to fifth training "training 5". The order of plural kinds of training in this training menu is defined. The plural kinds of training are subjected to ordering and displayed in a column as a list. Information on explanation of the content (content explanation information) of training and a button "training" are displayed for each kind of training in the training menu. The generating apparatus 1 first causes the user to carry out the first training "training 1". For that reason, the button "training" for the first training "training 1" is first displayed in a selectable state, but the buttons "training" for the other kinds of training are displayed in an unselectable state. The user selects the button "training" for the first training "training 1". The generating apparatus 1 causes the terminal device 4 to shift to a training screen corresponding to the selected training (which will be described later). After training in a state that the training screen is displayed, the display screen returns to this training menu screen. Similarly, training in a state that the corresponding training screen is displayed can be carried out for each kind of training. In a case where all kinds of training in the training menu are terminated, a message such as "all training is terminated." is displayed in the training menu screen. Then, an operation button such as "training again" or "measure and evaluate (display a result)" is set to a selectable display state.

The button "training again" is used in a case where the content of this training menu is repeatedly carried out again. In a case where this button is selected, the generating apparatus 1 causes the user to repeatedly carry out the same training menu from the first training in the similar manner. The button "measure and evaluate (display a result)" is used in a case where training result information is displayed. In a case where this button is selected, the generating apparatus 1 carries out analysis and evaluation on the basis of the task measurement to create the training result data 45B, for example, and causes the terminal device 4 to display a training result screen in the similar form to that of the evaluation result screen shown in FIG. 13. In a button "terminate training menu" is selected, the generating apparatus 1 causes the terminal device 4 to shift to the initial screen.

A button "carry out another training" may be provided in the screen. In a case where this button is selected, the generating apparatus 1 generates a training menu other than the training menu first generated and displayed as variation, and displays the generated training menu. As the other training menu, for example, a different training item may be selected, or a detailed parameter value may be changed in the same training item.

[Display Screen (5)—Training]

FIG. 15 shows a training screen as an example of the display screen of the terminal device 4. This training screen is a training screen for carrying out the first training "training 1" in the training menu shown in FIG. 14. The content explanation information, the detailed parameter value and the like for the first training are displayed on the training screen. For example, a message such as "Let's carry out finger tap by one hand accurately at pace of once every one second. (duration time: 30 seconds)" is displayed. A teaching waveform 1501 corresponding to training content is displayed on the training screen as teaching information for teaching the training content. For example, the teaching waveform 1501 is displayed on a graph 1500 in which a horizontal axis denotes a duration time and a vertical axis denotes a distance for each of a left hand and a right hand. The user selects a button "start training" when to start training, and carries out a finger tap at timing in accordance with the teaching waveform 1501 during the training. During the training, a measured waveform 1502 corresponding to a waveform signal while measuring is displayed in a state where the measured waveform 1502 is superimposed on the teaching waveform 1501 of the graph 1500. Further, auditory stimulation 1503 and/or visual stimulation 1504 may be displayed as the teaching information. The auditory stimulation 1503 is metronome audio based on frequency of the exercise, for example. The visual stimulation 1504 is lamp flickering display based on the same frequency.

Operation buttons such as "start training", "restart training", or "terminate training" are provided in the training screen. In a case where the user wants to restart the same training, the user selects the operation button "restart training", and restarts the same training from the beginning. The measuring apparatus 3 measures the exercise in response to it again. In a case where the user terminates this training, the user selects the operation button "terminate training". The measuring apparatus 3 transmits training measured data to the generating apparatus 1 in response to it.

The first training is training that emphasizes accuracy of rhythm of an exercise at a pace of 1 Hz. The more timing of the measured waveform 1502 coincides with timing of the teaching waveform 1501 with 1 Hz, in other words, the smaller variation in a tap interval is, the higher the evaluation value of the index item C (rhythmicity) becomes.

FIG. 16 shows a training screen for second training "training 2". Hereinafter, explanation for the same portions as those in the training screen shown in FIG. 15 will be omitted. The second training is training that emphasizes speed of an exercise at a pace of 3 Hz. The higher the speed of a measured waveform with respect to a teaching waveform is, the higher the evaluation value of the index item A (amount of exercise) becomes.

Figure 17:
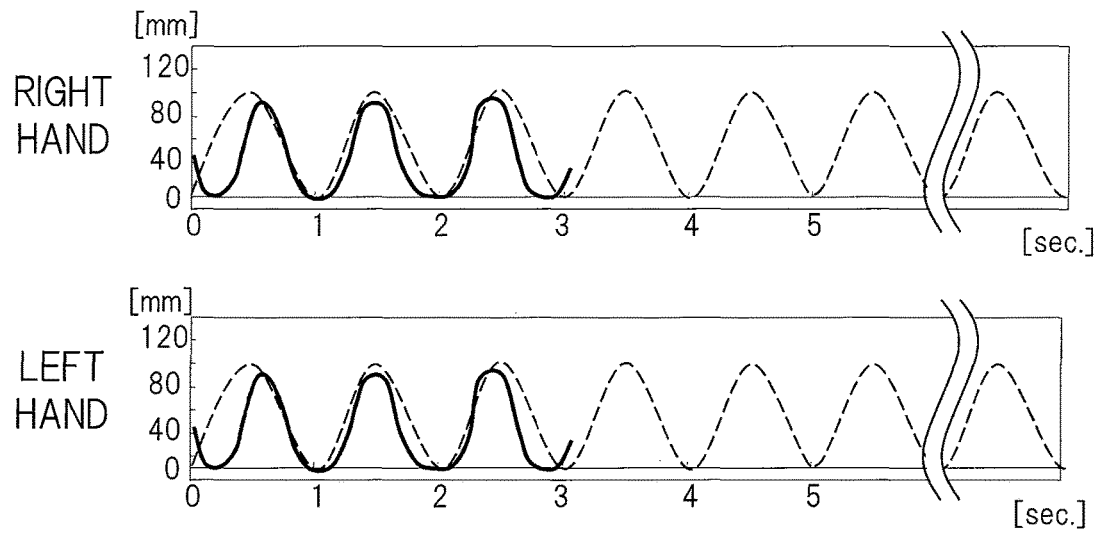
FIG. 17 is a view showing a third training screen as an example of the display screen according to the first embodiment.

FIG. 17 shows a training screen for third training "training 3". The third training is training that emphasizes cooperativeness of right and left hands in an exercise. The more measured waveforms of the right and left hands respectively match with teaching waveforms, the higher the evaluation value of the index item D (cooperativeness of both sides) becomes. Each of the first training to the third training is training for base strengthening regarding the single index item.

Figure 18:
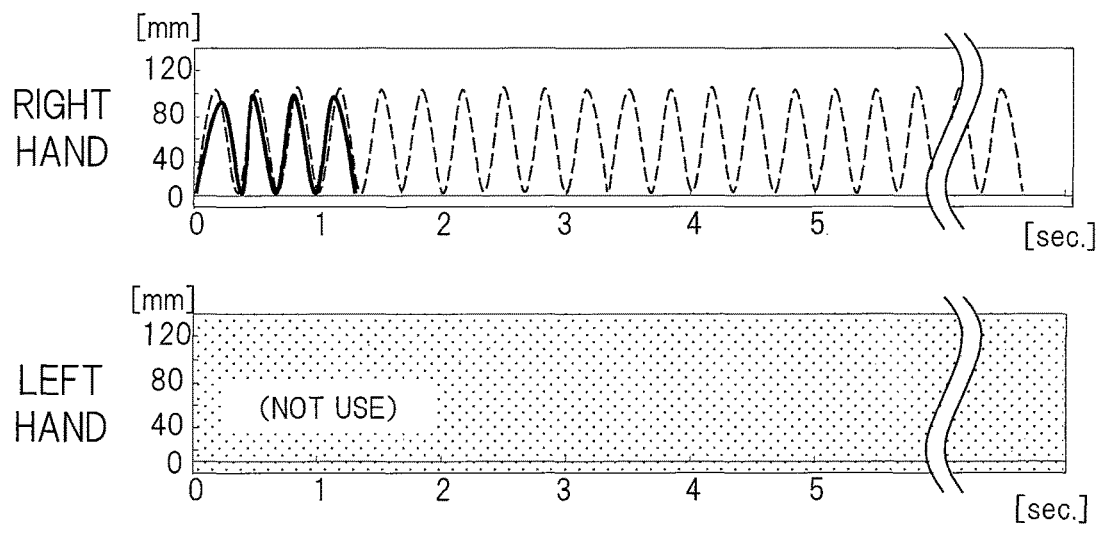
FIG. 18 is a view showing a fourth training screen as an example of the display screen according to the first embodiment.

FIG. 18 shows a training screen for fourth training "training 4". The fourth training is an example of applied training by a combination of two index items (C) and (A), and is training that emphasizes two of accuracy and speed of rhythm in the exercise. In other examples, the fourth training may be training by a set of index items (C) and (D), or training by a set of index items (A) and (D).

FIG. 19 shows a training screen for the fifth training "training 5". The fifth training is an example of application and finishing training by a combination of three index items including (C), (A), and (D), and is training that emphasizes three of accuracy, speed, and cooperativeness of both hands of rhythm in the exercise.

As the example described above, it is possible to effectively improve the exercise function and the like of the user through the plural kinds of training in the training menu. Further, the user may terminate the training in the middle of the training menu.

[Display Screen (6)—Training Result]

The generating apparatus 1 causes the terminal device 4 to display a training result screen in the similar manner to the evaluation result screen shown in FIG. 13 as described above after the training in the training menu is terminated. In the evaluation result screen shown in FIG. 13, the frame line 1302 is an example in which an analysis evaluating result through task measurement after training this time is displayed. By means of an on state of a button "overwrite past results", the evaluation result screen is displayed in a state where the frame line 1302 of a training result this time is superimposed on the frame line 1301 of the analysis evaluating result before the training this time. In an off state of the same button, only a frame line indicating the latest result is displayed. In the frame line 1302 of the training result, compared with the frame line 1301 before the training, the evaluation values of the index items (C), (A), and (D) are improved, and the evaluation values of the index items (B) and (E) are the same levels. An evaluation comment regarding the training result may be displayed in addition to the frame line 1302. For example, a message such as "(C), (A), and (D) are improved by training this time" is displayed.

The evaluation values of the index items that indicates the state of the user such as the exercise function are displayed as graphs on the training result screen. Therefore, the user easily recognizes his or her state and a training effect, and easily understands training significance. The overwriting display allows the user to compare states before and after the training, and the user can obtain feedback in time series. Therefore, the user easily recognizes the training effect and the like. The user also easily recognizes an item or items that was/were improved and an item or items that was/were not improved from the graph and the evaluation comment.

[Effects and the Like]

As described above, according to the finger exercise training menu generating system of the first embodiment, it is possible to support training of the user by generating and presenting the suitable training menu for the finger exercise to maintain or improve the cognitive function, the exercise function and the like of the user.

The following examples are given as a finger exercise training menu generating system according to a modification example of the first embodiment.

Modification Example (1)

As a modification example, the finger exercise training menu generating system may be configured so as to omit a task process at Step S9 in the processing flow shown in FIG. 7. In this configuration, the controller 101 directly determines an exercise function of a user on the basis of training measured data 45A stored at Step S7 after measurement of training in a training menu, for example, calculates an evaluation value for each index item, and creates training result data 45B.

Further, as a modification example, a process to generate a next training menu may be provided immediately after Steps S9 and S10 in the processing flow shown in FIG. 7 as well as Step S6. The controller 101 stores data on the next training menu generated by the process in training menu data 44. In this configuration, it is possible to omit the processes at Steps S2 to S6 when the user carries out next training, and this makes it possible to display the next training menu immediately, whereby the user can carry out the training.

Modification Example (2)

The generating apparatus 1 manages, by means of the user information manager 11, history information regarding actual results of past training multiple times for each user in the user information 41 of the DB 40. The controller 101 accumulates the analysis evaluating data 43 and the like of training each time in the DB 40, thereby allowing the user to refer to them. The training menu processor 14 generates the latest training menu on the basis of determination of actual result information on past training multiple times for each user. The training menu processor 14 calculates statistics such as average values in the past training multiple times for the individual user in every predetermined feature amount or every index item, for example. The training menu processor 14 determines training items and detailed parameter values of a next training menu on the basis of the statistics.

Further, in the overwriting display of the graph on the evaluation result screen shown in FIG. 13, the analysis evaluating results regarding the past training multiple times may be displayed so as to be superimposed thereon on the basis of history information of the user information 41. Further, the statistics of the index items of the user may be displayed on the evaluation result screen.

Further, the generating apparatus 1 may create a schedule of future training multiple times for each user (for example, patient). The training menu processor 14 creates a training menu for future training multiple times and a schedule thereof including the date and time of implement thereof on the basis of the analysis evaluating data 43 this time. The training menu processor 14 stores information on the created schedule in the user information 41. The user information manager 11 confirms the schedule of the user information 41 when to utilize the service, and confirms a training menu this time. Further, the user information manager 11 automatically confirms the schedule of the user information 41. In a case where it is the date and time of implement thereof, the user information manager 11 may notify it of the terminal device 4 or other user terminals to encourage the user to carry out training.

As examples to set the schedule of the future training multiple times, the date and time of implement a training item may be set to one week after or two weeks after. Further, a detailed parameter value each time, for example, a pace may variably be set to 1 Hz or 1.5 Hz.

Modification Example (3)

In a case where the user continuously carries out training multiple times for a predetermined time, a training menu to quantitatively apply a load to the user by training may be provided to the user. This makes it possible to heighten a training effect and improve the exercise function and the like. According to previous study, in exercise learning, it is possible to extract performance from the user by giving a little difficult target to the user. For example, performance of the user such as a current exercise function is indicated by 100%. In such a case, a target value corresponding to 90%, 100%, 110%, 120%, 130% or the like is given to the user as a target value of an exercise. In the case where the target value is 110%, for example, the maximum performance seems to be exerted. By repeatedly continuing such setting for the target value, it can be expected that performance of the user is heightened.

The training menu processor 14 manages a quantitative load of the training item of the training menu. The training menu processor 14 variably sets a target value of the training described above in accordance with a state of the user. For example, in relation to an index item of a given exercise function and a training item corresponding to it, performance expressed by a current evaluation value of the user is indicated by 100%. In such a case, a target value is set to 110% as a target value of next training of the same index item. For example, in training of a user, one-hand free run with a duration time of 15 seconds is measured, and "the number of times of taps" is 30 times (at a pace of 2 Hz) as a feature amount thereof. In next training, 110% as a target value, that is, 33 times (at a pace of 2.2 Hz) is set as "the number of times of taps". The pace of a teaching waveform during training becomes 2.2 Hz. Note that video in which an exercise by which a target value is achieved is recorded may be displayed as teaching information corresponding to the target value.

The training menu processor 14 sets the detailed parameter value of the training item corresponding to the target value described above. The training menu processor 14 creates the training menu including the setting of the target value described above and a schedule thereof. The training menu processor 14 determines a degree of achievement of the target value in a training result and stores the degree of achievement. In a case where an evaluation value of a previous training result is worse compared with the target value, the training menu processor 14 may reduce a target value of next training by a predetermined rate. In a case where the evaluation value of the previous training result is better compared with the target value, the training menu processor 14 may adjust a next target value so as to be raised by a predetermined rate.

Second Embodiment

A finger exercise training menu generating system according to a second embodiment of the present invention will be described with reference to FIG. 20 to FIG. 26. A basic configuration according to the second embodiment is similar to that of first embodiment. Hereinafter, different portions in the configuration according to the second embodiment from the configuration of the first embodiment will be described.

[System (2)]

Figure 20:
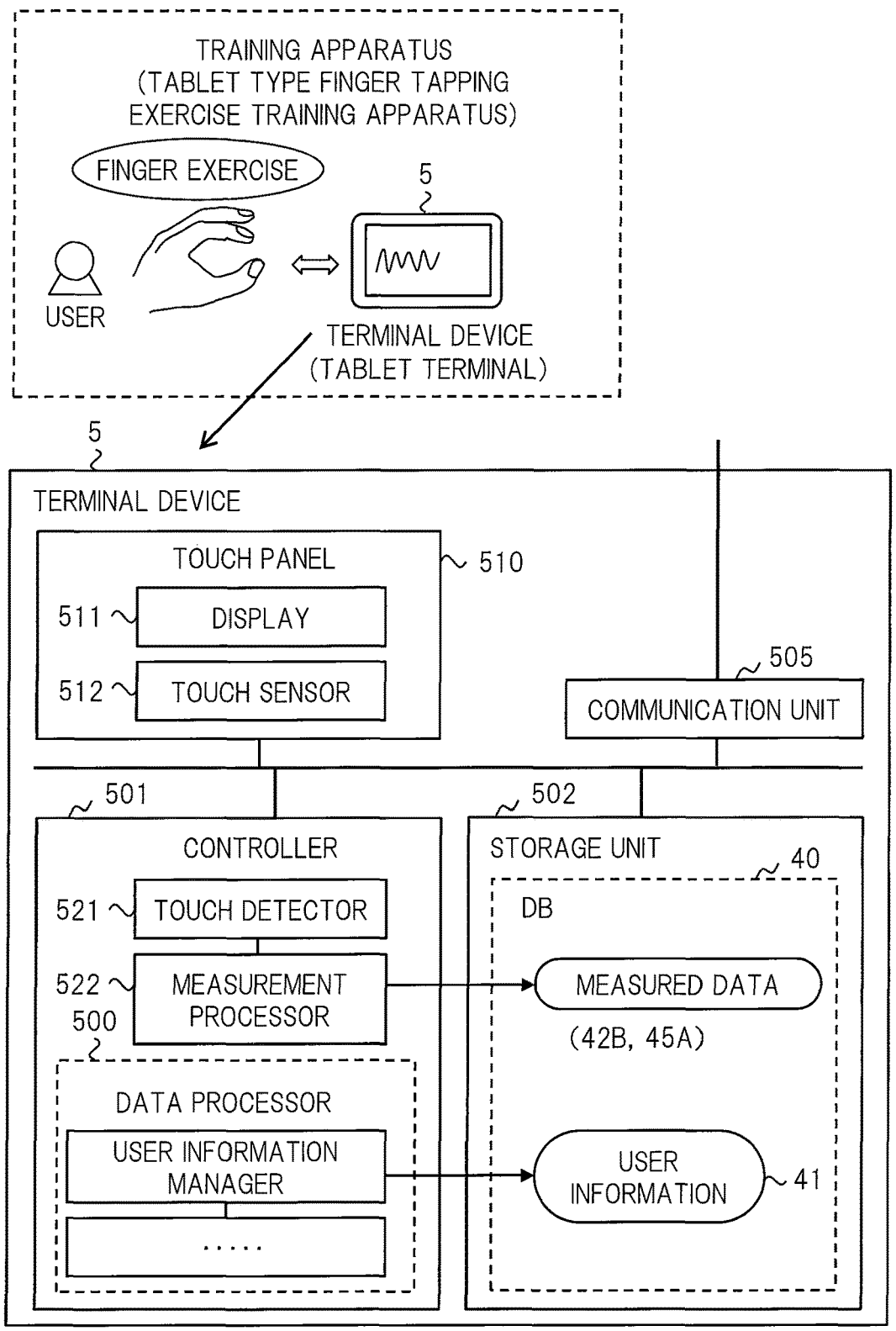
FIG. 20 is a view showing a finger exercise training menu generating system according to a second embodiment of the present invention.

FIG. 20 shows a configuration of a finger exercise training system that includes a finger exercise training menu generating system according to the second embodiment. The finger exercise training system is provided in facilities, a user's home, or the like. The finger exercise training menu generating system according to the second embodiment uses a training apparatus that is a tablet type finger tapping exercise training apparatus. This training apparatus is constructed by a terminal device 5 that is a tablet terminal. In the second embodiment, exercise measurement and information display are carried out by using a touch panel included in the terminal device 5. The second embodiment corresponds to a configuration in which the measuring function of the measuring apparatus 3 and a display function of the terminal device 4 according to the first embodiment are integrated into one terminal device 5. The terminal device 5 may be an apparatus that is installed in facilities, or an apparatus that is possessed by a user.

The terminal device 5 includes a controller 501, a storage unit 502, a communication unit 505, a touch panel 510, and the like. They are connected to each other via a bus. The touch panel 510 includes a display 511 and a touch sensor 512. The display 511 is a liquid crystal display or an organic EL display, for example, and has a display screen. The touch sensor 512 adopts an electrostatic capacity system, for example, and is arranged in an area corresponding to the display screen. The touch sensor 512 detects a change in electrostatic capacity based on a state of approach or contact of a finger with respect to the display screen as an electric signal, and outputs a detected signal to a touch detector 521.

The controller 501 controls the whole terminal device 5, and is constructed by a CPU, a ROM, a RAM and the like. The controller 501 realizes a data processor 500 to execute a finger exercise training menu generating process and the like on the basis of software program processing. A configuration of the data processor 500 is substantially similar to that according to the first embodiment. The controller 501 further includes the touch detector 521 and a measurement processor 522. The controller 501 realizes a function to obtain measured data through the touch panel 510, a function to process and analyze the measured data, a function to output information to the display screen of the display 511 in the touch panel 510. The touch detector 521 carries out a process to detect, as a touch position coordinate and the time-series signal, a state of approach or contact of a finger of the user on the display screen and a state of a motion of the finger on the basis of a detected signal from the touch sensor 512. The measurement processor 522 measures the position and the motion of the finger on the display screen as a waveform signal by using detection information of the touch detector 521, and obtains the waveform signal as measured data. The measured data correspond to the task measured data 42B or the training measured data 45A. The data processor 500 generates a training menu on the basis of the measured data by the similar process to that according to the first embodiment, and displays the generated training menu on the display screen of the display 511. Further, the data processor 500 creates analysis evaluating data and the like to display an evaluation screen or the like on the display screen of the display 511.

Example (1) of Exercise and Display Screen

Figure 21:
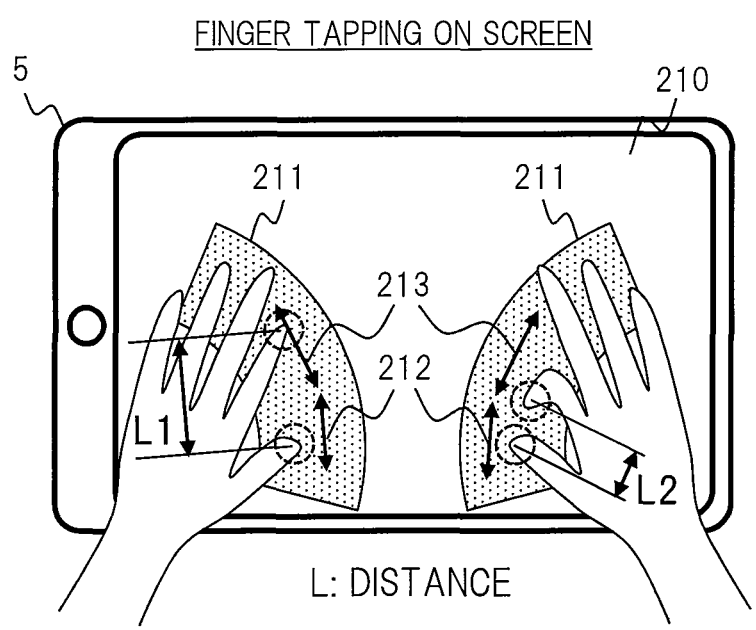
FIG. 21 is a view showing finger tapping on a screen as an exercise example according to the second embodiment.

FIG. 21 shows a method of carrying out an exercise for a finger tapping on a display screen 210 of the terminal device 5. The terminal device 5 may provide a task or training in which this method is used. In this method, the controller 501 displays, on a background region of the display screen 210, a region 211 for arranging target two fingers of each of both hands. FIG. 21 shows the case where a first finger is a thumb and a second finger is a forefinger as the target two fingers, for example. The user arranges the four fingers in a state that the two fingers of each hand contact or approach the region 211. Although it depends on the touch sensor 512 and the like, in the present embodiment, the user is caused to basically maintain, during this exercise, a state that the fingers touch the region 211 of the display screen. The user carries out finger tapping to cause the two fingers of each hand to open and close on the region 211. The terminal device 5 measures the exercise for the finger tapping through the touch sensor 512 and the like, and obtains the measured data such as the waveform signal as well as the first embodiment. A motion 212 of the first finger and a motion 213 of the second finger on the region 211 are respectively shown by arrows. As a distance L between tips of the two fingers, a distance L1 at a left-hand side and a distance L2 at a right-hand side are shown.

Figure 22:
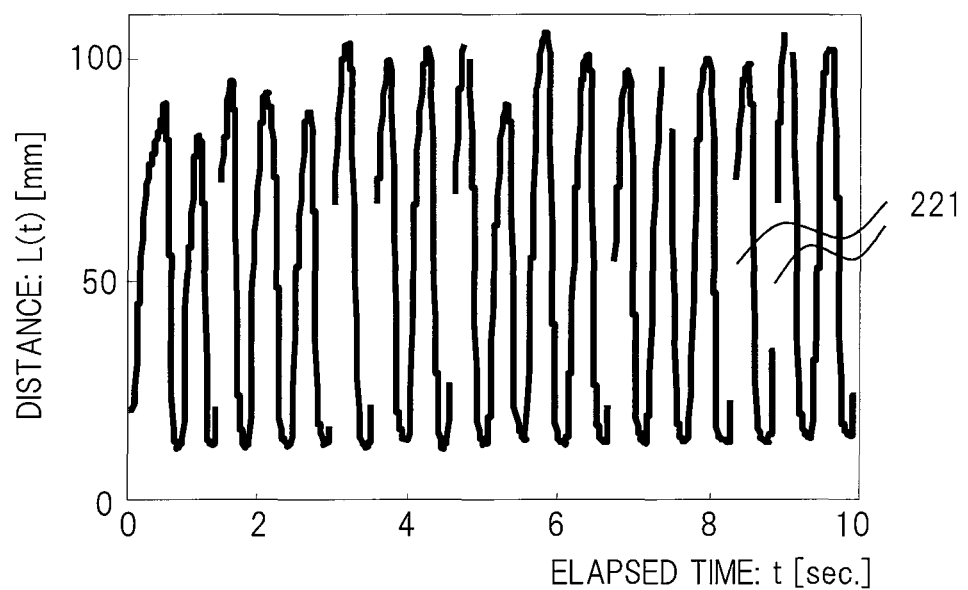
FIG. 22 is a view showing a waveform of a distance between two fingers during the finger tapping on the screen according to the second embodiment.

FIG. 22 shows a waveform signal of the distance L between the two fingers as an example of measured data corresponding to the exercise for the finger tapping in FIG. 21. A horizontal axis denotes an elapsed time t [sec.], and a vertical axis denotes a distance L (t) [mm] per the elapsed time t. Note that each of portions 221 in a waveform denotes a portion at the time of a state that the corresponding finger moves away from the region 211 to an extent. In the similar method to that according to the first embodiment, the terminal device 5 extracts a feature amount on the basis of the measured data; calculates an evaluation value of an index item; generates a training menu; and presents the generated training menu.

Example (2) of Exercise and Display Screen

FIG. 23 shows a reaching method as an example of another exercise for finger tapping and a display screen thereof. The terminal device 5 may provide a task or training using the reaching method. (a) of FIG. 23 shows cross reaching. A figure 231 of an initial position is first displayed on the display screen 210 of the terminal device 5. Measurement is started in a state where a target finger, for example, a forefinger is placed on the figure 231 of the initial position. After the start, a figure 232, for example, a cross as a target corresponding to a marker is displayed on the display screen 210. The controller 501 displays the figure 232 at a different position at a predetermined cycle, for example. The user carries out a finger tap so as to track a position of the figure 232 by stretching the finger. In the present embodiment, a state where a finger tap is carried out at a position 233 having a gap with respect to a central position of the figure 232. There is a distance E corresponding to the gap between the central position of the figure 232 as the target and the tapped or touched position 233. The terminal device 5 calculates the distance E, a delay time TD or the like on the basis of measured data as one of feature amounts. The delay time TD is a time from a point of time when the figure 232 as the target is displayed in a waiting state that the finger is placed on the figure 231 of the initial position to a point of time when the finger touches the figure 232 as the target. A predetermined index item, for example, marker trackability or accuracy is associated with the feature amount such as the distance E. For example, an exercise to touch a figure of the marker as quickly as possible, that is, with a shorter delay time as much as possible is set to an index item of the marker trackability as a training item. An exercise to touch the figure at a position as accurate as possible, that is, with a small gap is set to an index item of the accuracy as the training item.

(b) of FIG. 23 shows circle reaching. A circular area is displayed as a figure 234 of a target. The user similarly carries out a finger tap to the inside of the circular area of the FIG. 234. A distance between a central position of the figure 234 and a tap position is extracted as a feature amount, for example.

Example (3) of Exercise and Display Screen

FIG. 24 shows a continuously touching method as an example of still another exercise for finger tapping and a display screen thereof. The terminal device 5 may provide a task or training using the continuously touching method. (a) of FIG. 24 shows a continuous touch by one hand. A figure 241, for example, a circular area for touch of a thumb of a left hand is displayed at one location on the display screen 210, for example, in the vicinity of lower left of the display screen 210. The user touches the displayed figure 241 by one finger and continuously touches the figure 241. In a case where the FIG. 241 becomes a non-display state, the user lifts the finger from the figure 241. The controller 501 controls display of the figure 241. For example, the controller 501 switches between a display state and the non-display state of the figure 241 at a predetermined cycle, and displays the figure 241 the predetermined number of times. Further, auditory stimulation or the like may be given to the user as teaching information together with the display of the figure 241. The number of times of touch to the figure 241, a touch interval, a touch delay time and the like are extracted as feature amounts, for example.

(b) of FIG. 24 shows a continuous touch by both hands at the same time. Figures 242 each indicating a touch position of a target finger each of a left hand and a right hand are displayed at two locations on the display screen 210. The user continuously touches the displayed figures 242 at the same timing by both hands at the same time. Similarly, an alternately continuous touch by both hands can be carried out. In such a case, the controller 501 switches the display so that the right and left figures 242 are displayed alternately. The user touches the figures 242 by the right and left hands at alternate timing. A phase difference of touch on the right and left figures 242 and the like are extracted as feature amounts, for example. A predetermined index item, for example, cooperativeness of both sides or the like is associated with the feature amount. In the case of the continuous touch by both hands at the same time, an ideal value of the phase difference is 0°. In the case of the continuous touch by both hands alternately, the ideal value of the phase difference is 180°. For example, an exercise to touch the right and left figures 242 in the same phase as much as possible is set to an index item of the cooperativeness of both sides as a training item.

As another example of the exercise, auditory stimulation or the like may be outputted as teaching information without displaying any figure. For example, two kinds of voices may be outputted at a time to touch the display screen and a time not to touch the display screen in a predetermined cycle or the like.

Example (4) of Exercise and Display Screen

FIG. 25 shows a tapping method in accordance with light as an example of still another exercise for finger tapping and a display screen thereof. The terminal device 5 may provide a task or training using this method. (a) of FIG. 25 shows a tap by one hand. A figure 251 for a tap of a target finger of a left hand and a figure 252 are displayed on the display screen 210. The figure 252 becomes light for visual stimulation, which indicates timing of tapping the FIG. 251. The controller 501 carries out flickering display so as to switch a display state and a non-display state of the figure 252. The user taps the figure 251 for tapping at timing when the figure 252 is displayed. As another example of the exercise, a sound that is auditory stimulation may be outputted in place of the figure 252 for visual stimulation, or a method of carrying out a continuous touch may be adopted. As a feature amount, there is a time deviation of points of time of a tap or touch with respect to points of time of periodic generation of stimulation, for example. This time deviation corresponds to a delay time from a point of time when the figure 252 is displayed to a point of time when the figure 251 is tapped. Similarly, (b) of FIG. 25 shows the case of taps by both hands at the same time. Two figures 251 for tapping are provided at right and left portions of the display screen, and flickering display of two right and left figures 252 for visual stimulation is carried out at the same timing. Similarly, in the case of a tap by both hands alternately, the controller 501 carries out flickering display of the two right and left figures 252 at alternate timing.

Example (5) of Exercise Display Screen

Figure 26:
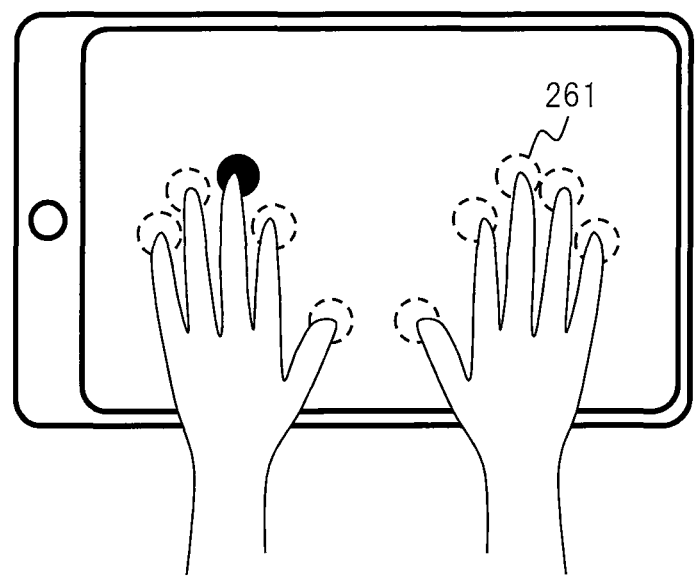
FIG. 26 is a view showing a five-finger tap as an exercise example according to the second embodiment.

FIG. 26 shows a five-finger tapping system as an example of still another exercise for finger tapping and a display screen thereof. The terminal device 5 may provide a task or training using the five-finger tapping system. In this method, five fingers of a target hand are used. The terminal device 5 displays figures 261 for tapping by five fingers of each of both hands, that is, the total ten fingers on a background region of the display screen 210. The user first places the five fingers on the display screen 210 so as to touch the display screen 210. The terminal device 5 automatically adjusts and sets a display position of each of the figures 261 on the basis of detection of touch positions thereof. The terminal device 5 controls display of the figure 261 at each position. The terminal device 5 sets the figure 261 at a position to be tapped to a specific display state (illustrated by a black circle, for example), and sets the other figures 261 at positions not to be tapped to another display state. The terminal device 5 controls switching of the display states of each of the figures 261. The user taps the figure 261 by the corresponding finger in accordance with display of the figure 261 to be tapped. In this method, various kinds of index items for each finger of the five fingers can be evaluated. As a result, it is also possible to determine which finger is to be improved particularly. The controller 501 may determine a target finger for training in accordance with the determination, and generate a training menu including training for the target finger.

[Feature Amount]

An example of association between a specific feature amount and an index item in the second embodiment is as follows.

As feature amount parameters regarding the reaching method, there are the following parameters. A parameter (2-1) "average value of delay times from target display" [sec.] is an average value of the delay times described above. Each of parameters (2-1) and (2-2) is associated with an index item h1 (which will be described later). The parameter (2-2) "standard deviation of delay times from target display" [sec.] is a standard deviation regarding the delay time described above.

A parameter (2-3) "average value of position errors with respect to target" [mm] is an average value of the distances E described above. Each of parameters (2-3) and (2-4) is associated with an index item i1. The parameter (2-4) "standard deviation of position errors with respect to target" [mm] is a standard deviation regarding the distance E described above.

As feature amount parameters regarding a continuously touching method by one hand, there are parameters including (2-5) "the number of times of taps" [-], (2-6) "average of tap intervals" [sec.], (2-7) "tap frequency" [Hz], (2-8) "standard deviation of tap interval" [sec.], (2-9) "coefficient of variation of tap interval" [-], (2-10) "variation in tap interval" [mm$^2$], (2-11) "degree of distortion of tap interval distribution" [-], (2-12) "standard deviation of regional tap interval" [sec.], (2-13) "tap interval attenuation rate", and the like. The definition of each feature amount is similar to that according to the first embodiment. The parameter (2-5) is associated with an index item a1. Each of the parameters (2-6) to (2-12) is associated with an index item c1 and an index item f1. The parameter (2-13) is associated with an index item b1.

As feature amount parameters regarding a continuously touching method by both hands, there are the following parameters. A parameter (2-14) "average of phase differences" [°] is an average value of the phase differences such as touch by both hands. A parameter (2-15) "standard deviation of phase difference" [°] is a standard deviation of the phase difference described above. Each of the parameters (2-14), (2-15) is associated with an index item d1 and an index item g1.

As feature amount parameters regarding a method of touching or tapping in accordance with light stimulation or auditory stimulation, there are the following parameters. A parameter (2-16) "average value of time deviations against stimulation" [sec.] is an average value of the time deviations described above. A parameter (2-17) "standard deviation of time deviation against stimulation" [°] is a standard deviation of the time deviations described above. Each of the parameters (2-16) and (2-17) is associated with an index item e1.

[Index Item and Training Item]

As examples of a specific index item and examples of association with a training item according to the second embodiment, there are the following ones. As the index items, there are index items including (a1) "amount of exercise", (b1) "endurance", (c1) "rhythmicity", (d1) "cooperativeness of both sides", (e1) "trackability", (f1) "speed control", (g1) "independent control of both hands", (h1) "agility", (i1) "accuracy", and the like. The index item a1 to the index item g1 are substantially similar to the index item A to the index item G according to the first embodiment.

The index item h1 "agility" is agility when a finger of the user touches a figure of a marker. Examples of training items associated with this index item h1 areas follows. This training item is an exercise to touch a figure for previous notice by displaying the figure for previous notice before displaying a target figure, and then displaying the target figure. Another training item is an exercise to touch a target figure by outputting auditory stimulation at the same time as display of the target figure.

The index item i1 "accuracy" is accuracy of a position when the finger touches the figure of the marker. An example of a training item associated with this index item i1 is as follows. In this training item, a circular area or the like is displayed as a figure, and the user is caused to touch an area within a fixed distance range from a central position of the figure. In a case where the area is touched by a finger of the user, predetermined auditory stimulation or the like is outputted.

[Effects and the Like]

As described above, according to the finger exercise training menu generating system of the second embodiment, it is possible to support training of the user by generating and present the suitable training menu for the finger exercise as well as the first embodiment. In the second embodiment, there is no need to provide the motion sensor 20 or the like in particular.

Third Embodiment

A finger exercise training menu generating system according to a third embodiment of the present invention will be described with reference to FIG. 27 to FIG. 29. A basic configuration according to the third embodiment is similar to that of the first embodiment. Hereinafter, different portions in the configuration according to the third embodiment from the configuration of the first embodiment will be described.

[System (3)]

Figure 27:
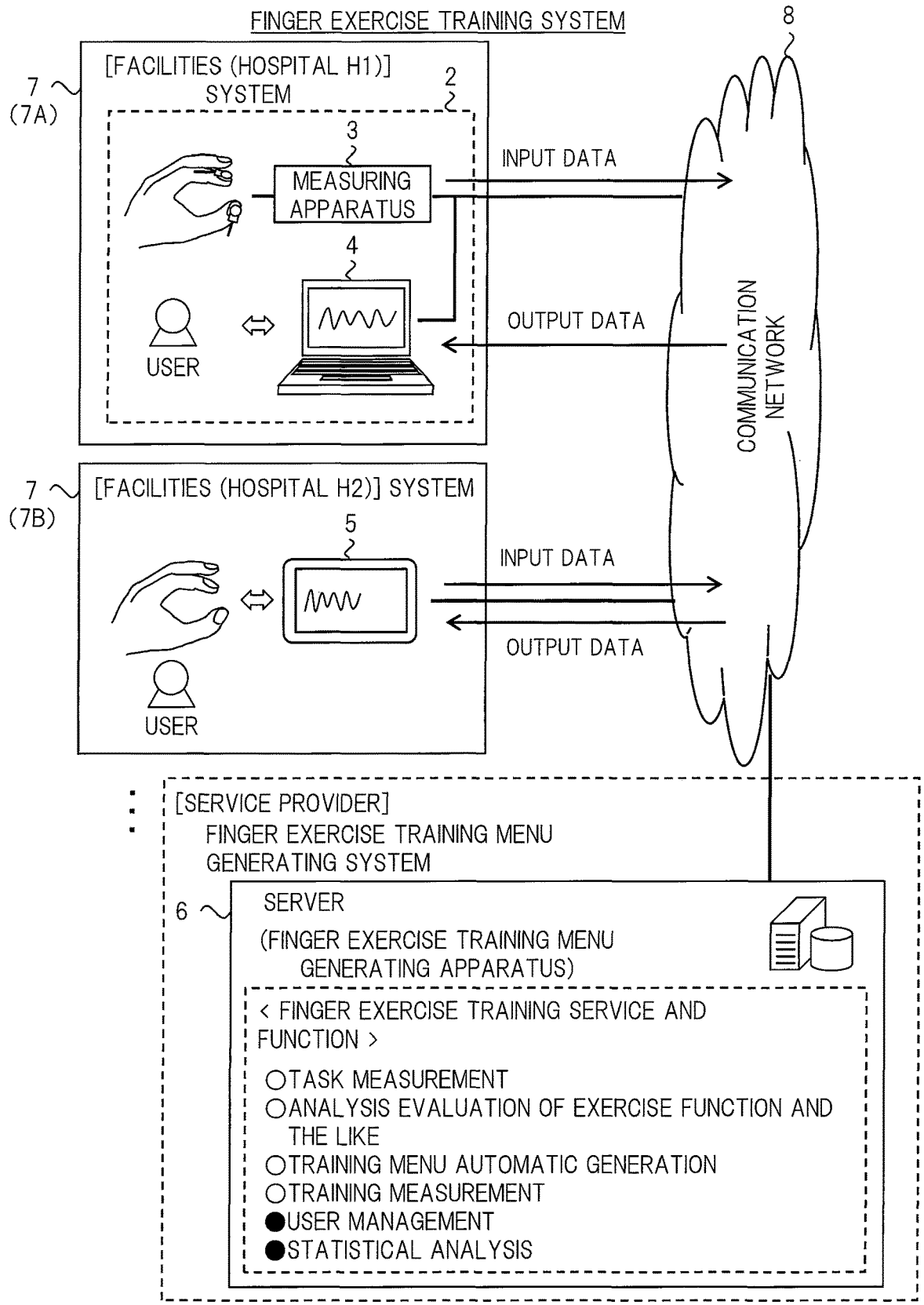
FIG. 27 is a view showing a configuration of a finger exercise training menu generating system according to a third embodiment of the present invention.

FIG. 27 shows a configuration of a finger exercise training system that includes a finger exercise training menu generating system according to the third embodiment. The finger exercise training system includes a server 6 of a service provider, and systems 7 for a plurality of facilities. They are connected to each other via a communication network 8. Each of the communication network 8 and the server 6 may be configured to include a cloud computing system. The finger exercise training menu generating system according to the third embodiment is mainly constructed by the server 6. The server 6 corresponds to a finger exercise training menu generating apparatus. The server 6 provides finger exercise training service to the systems 7 for the plurality of facilities.

Each of the facilities may be any of various kinds of a hospital or a medical examination center, public facilities, amusement facilities, or user's home, and the like. The system 7 is provided in each of the facilities. The system 7 includes a training apparatus as described above. As examples of the system 7 for the facilities, there are a system 7A for a hospital H1, a system 7B for a hospital H2, and the like. For example, the system 7A for the hospital H1 includes a measuring apparatus 3 and a terminal device 4, which constitutes a training apparatus 2, as well as the first embodiment. The system 7B for the hospital H2 includes a terminal device 5, which constitutes a training apparatus, as well as the second embodiment. The configuration of each system 7 may be the same as each other, or different from each other. The system 7 of the facilities may include an electronic health record managing system for a hospital, and the like. The training apparatus of the system 7 may be a dedicated terminal. A user who is in the facilities is allowed to carry out training for a finger exercise by using the training apparatus.

The server 6 is an apparatus managed by a service provider. The server 6 has a function to provide finger exercise training service similar to that by the generating apparatus 1 according to the first embodiment to facilities and users as service based on information processing. The server 6 provides service processing by a client/server system to the training apparatus of the system 7. The server 6 has a user managing function, a statistical analysis function and the like in addition to such a function. The user managing function is a function to register and accumulate user information of each of a group of users, measured data, analysis evaluating data and the like, which are obtained through the systems 7 of the plurality of facilities, in a DB, and manage them. The statistical analysis function is a function to carry out statistical processing and analytical processing regarding the group of users on the basis of the user information and the analysis evaluating data of the group of users. The server 6 generates the optimum training menu for each user by using statistical analysis results. Note that the terminal device 5 according to the third embodiment does not require a function to generate a training menu by itself, and has a measuring function using a touch panel and a display function to display the training menu generated by the server 6 and the like.

[Server]

Figure 28:
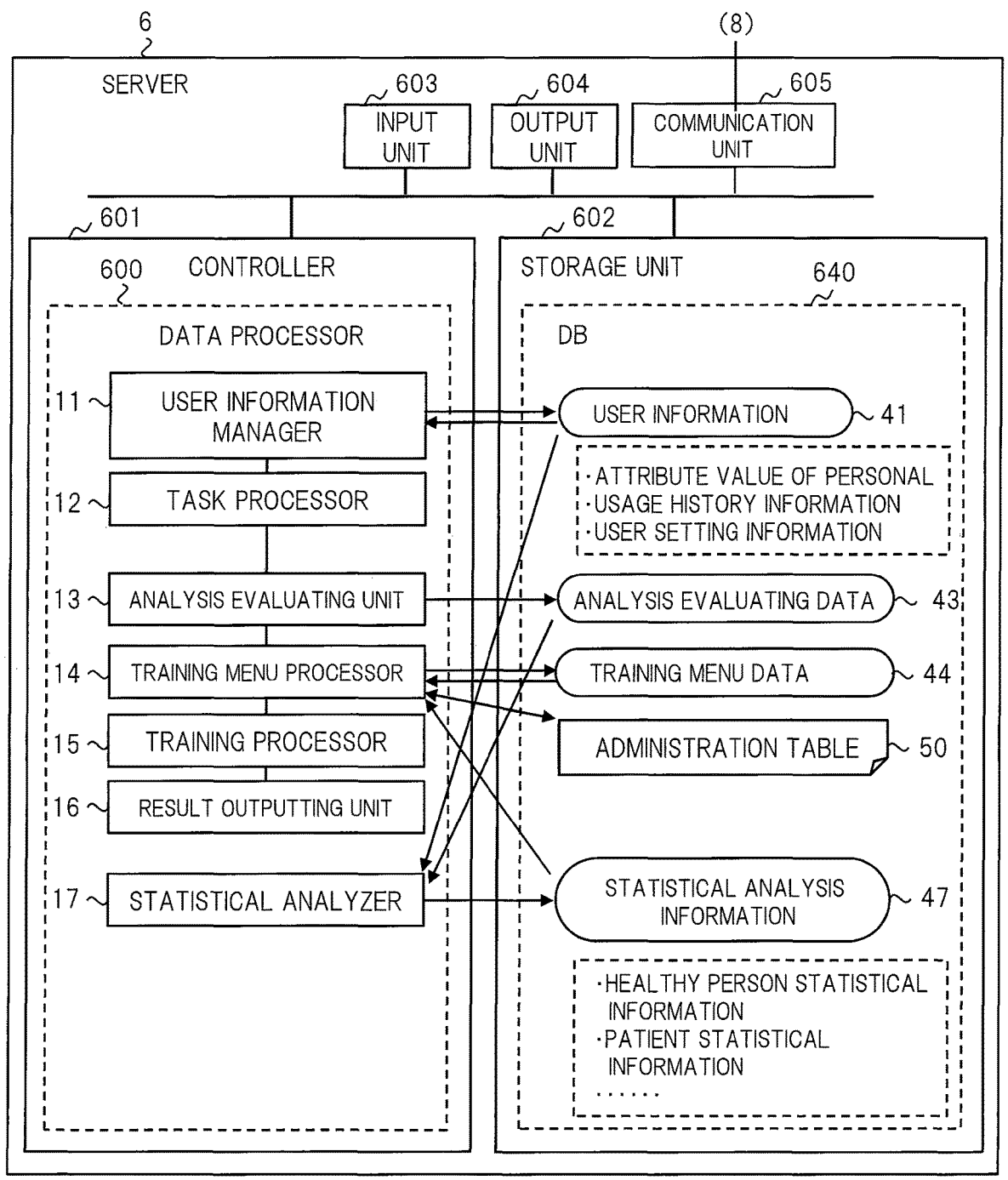
FIG. 28 is a view showing a configuration of a server that is a finger exercise training menu generating apparatus according to the third embodiment.

FIG. 28 shows a configuration of the server 6. The server 6 includes a controller 601, a storage unit 602, an input unit 603, an output unit 604, and a communication unit 605. They are connected to each other via a bus. The input unit 603 is a part to carry out an operational input by an administrator or the like of the server 6. The output unit 604 is a part to carry out display of a screen to the administrator or the like of the server 6. The communication unit 605 has a communication interface, and is a part to carry out communication processing with the communication network 8. A DB 640 is stored in the storage unit 602. The DB 640 may be managed by a DB server or the like other than the server 6.

The controller 601 controls the whole server 6, and is constructed by a CPU, a ROM, a RAM and the like. The controller 601 realizes a data processor 600 to execute a finger exercise training menu generating process and the like on the basis of software program processing. The data processor 600 includes a user information manager 11, a task processor 12, an analysis evaluating unit 13, a training menu processor 14, a training processor 15, a result outputting unit 16, and a statistical analyzer 17.

The user information manager 11 registers user information regarding the group of users of each of the systems 7 of the plurality of facilities in the DB 640 as user information 41 and manage the user information. The user information 41 contains an attribute value, usage history information, user setting information and the like of each individual user. The usage history information contains actual result information of training of each user past multiple times. The statistical analyzer 17 carries out statistical processing and analytical processing by using the user information 41, the analysis evaluating data 43 and the like, and stores statistical analysis information 47, which is a result of the processing, in the DB 640. The statistical analysis information 47 contains healthy person statistical information, patient statistical information and the like. The training menu processor 14 generates a training menu for each user while referring to the statistical analysis information 47, and stores the generated training menus in the DB 640 as the training menu data 44.

[Server Managing Information]

FIG. 29 shows a data configuration example of the user information 41 that the server 6 manages in the DB 640. This table for the user information 41 contains a user ID, a facilities ID, a user ID in the facilities, sex, age, disease, a severity score, a symptom, eyesight, hearing, history information, and the like. The user ID is unique identification information for each user in the present system. The facilities ID is identification information for each of facilities in which the corresponding system 7 is provided. Note that a communication address and the like of the training apparatus of each of the systems 7 are separately managed. The user ID in the facilities is user identification information in a case where the user identification information managed in the facilities or the system 7 exists. Namely, the user ID and the user ID in the facilities are managed so as to be associated with each other. As the disease item and the symptom item, a value indicating disease and/or a symptom selected and inputted by the user, or a value obtained by diagnosing the user in a hospital by a doctor or the like is stored. The severity score is a value indicating a degree regarding the disease.

The history information item is information for managing past service usage and actual results of training by the user. As the history information, information such as date and time of usage and training each time or whether training is carried out or not is stored in time series. Further, each of data in a case where the training was carried out that time, that is, data described above, such as task measured data, the analysis evaluating data, the training menu data, training measured data, or training result data, is stored in the history information item. Information on an address at which each of the data is stored may be stored in the history information item.

[Statistical Analysis Processing]

The statistical analyzer 17 refers to the user information 41 registered in the DB 640 at any time, carries out the statistical processing and the analytical processing, and creates the statistical analysis information 47. The statistical analyzer 17 refers to a group of users who are healthy persons, for example. Namely, the statistical analyzer 17 refers to data on users whose values indicating disease are not registered in the disease item as an attribute value in the user information 41 or users whose values indicating healthy are registered. The statistical analyzer 17 refers to an evaluation value of each index item in the analysis evaluating data 43 for the group of users, for example. The statistical analyzer 17 counts or compiles the evaluation values of each index item, calculates statistic thereof such as an average value, and stores data containing this statistic in the DB 640 as the healthy person statistical information. Further, the statistical analyzer calculates statistics as the healthy person statistical information, more particularly, in accordance with classification of the attribute value such as sex or age of the user. For example, there is classification of teenagers and twenties of male.

Similarly, the statistical analyzer 17 refers to a group of users who are patients, for example. Namely, the statistical analyzer 17 refers to data of users whose values indicating disease in the disease item are registered in the user information 41 as the attribute value. In particular, the group of users may be classified in accordance with classification of disease (for example, "motor impairment" or the like). The statistical analyzer 17 refers to an evaluation value of each index item in the analysis evaluating data 43 for the group of users with respect to the disease, for example. The statistical analyzer 17 counts or compiles the evaluation values of each index item, calculates statistic thereof such as an average value, and stores data containing this statistic in the DB 640 as the patient statistical information.

[Training Menu Generating Process]

The server 6 basically carries out the similar processes to those in the processing flow shown in FIG. 7 according to the first embodiment. The server 6 carries out a specific training menu generating process at Step S6. The server 6 generates the optimum training menu for each user on the basis of the user information 41 of the group of users and the statistical analysis information 47. In the third embodiment, the training menu for each user is generated by using results of analysis that is not based on a unit closed by an individual user, but based on a unit of a group of users including other persons. An example of a generating method is as follows.

The server 6 carries out the following process when a training menu for a first user is to be generated. The server 6 confirms a predetermined item of attribute values of the first user, for example, sex, age, or disease on the basis of the user information 41. The server 6 refers to information of another user who has attribute values similar to the sex, age, or disease of the first user, that is, the same attribute values or attribute values in the vicinity of a range of the corresponding attribute value of the first user. For example, the first user is a healthy person of female in her thirties like an example of a second row of the table shown in FIG. 29. The server 6 refers to statistical information of a group of users whose attribute values are similar to the attribute values of the first user for comparison from the DB 640. Here, the healthy person statistical information and the like have already been stored in the DB 640. The server 6 refers to statistical information corresponding to classification similar to the attribute value of the first user (female in her thirties) from the healthy person statistical information.

The server 6 picks up an index item whose evaluation value is low on the basis of the analysis evaluating data 43 of the first user, for example, as well as the first embodiment. When the picked-up index item is determined, the server 6 compares the evaluation value of each index item of the first user with statistics of the evaluation value of each index item in the statistical information obtained by being referred to from the DB 640. In a case where the evaluation value of the first user is smaller than the statistics on the basis of the comparison, the server 6 selects the index item, for example. As a result, the index items A and B are selected, for example. The server 6 makes up a training menu by using training items associated with the index items A and B as well as the first embodiment.

As another example, the first user is a patient having disease. The first user is a male in his fifties like an example of a first row of the table shown in FIG. 29, and "dementia" is stored in its disease item. The server 6 refers to statistical information regarding a portion of the corresponding disease in the patient statistical information regarding a group of users who have a similar attribute value (for example, "dementia" or disease classification containing it) to the attribute value of the disease of the first user from the DB 640. Similarly, the server 6 compares the evaluation value of each index item in the analysis evaluating data 43 of the first user with the statistics of evaluation values of each index item in the statistical information obtained by being referred to from the DB 640, and selects an index item to be picked up on the basis of a result thereof. The server 6 makes up a training menu by using training items associated with the selected index item. A method of comparing other attribute values in the user information 41 can be carried out in the similar manner.

As another method, the following can be adopted. The server 6 refers to those of other similar user with respect to the feature amounts and the evaluation values of the index items in the analysis evaluating data 43 of the first user. For example, a second user similar to the first user exists. The server 6 refers to training menu data and/or training result data of the second user. The server 6 makes up a training menu for the first user on the basis of a training menu for the second user. Further, the server 6 may determine training of a training item whose training effect is large on the basis of the training result data and the actual result information of the second user, and make up a training menu for the first user so as to include the training. Magnitude of the training effect can be determined from a change in the evaluation value.

[Effects and the Kike]

As described above, according to the finger exercise training menu generating system of the third embodiment, it is possible to support training of the user by generating and present the suitable training menu for the finger exercise as well as the first embodiment. In particular, in the third embodiment, by centrally managing information of a plurality of users and designing training on the basis of statistical analysis in view of statistics of a group of users, it is possible to provide a more suitable training menu to each user.

As a modification example of the finger exercise training menu generating system according to the third embodiment, the following configuration can be adopted. In the first to third embodiments, the generating apparatus 1, the terminal device 5, or the server 6 carries out the analysis evaluating process based on the task measurement, and creates the analysis evaluating data. As this modification example, the finger exercise training menu generating system may be configured so that an external device carried out a task measurement process and an analysis evaluating process and the analysis evaluating data are inputted thereto from the external device. For example, the server 6 obtains existing analysis evaluating data from the external device, and carries out the training menu generating process by using the analysis evaluating data.

As described above, the present invention has been explained specifically on the basis of the embodiments. However, the present invention is not limited to the embodiments, and the present invention may be modified into various forms without departing from the substance thereof.

REFERENCE SIGNS LIST

1 ... finger exercise training menu generating apparatus, 2 ... training apparatus, 3 ... measuring apparatus, 4 ... terminal device.

The invention claimed is:

1. A finger exercise training system comprising:
a pair of magnetic motion sensors configured to be worn by respective fingers of the user;
a processor coupled to the magnetic motion sensors and a memory, the processor configured to:
obtain measured data from the pair of magnetic motion sensors and store the measured data in the memory, the measured data is data of the finger exercise including movements of the fingers of the user and is a time-series waveform signal,
determine analysis evaluation data based on the measured data of the finger exercise, the analysis evaluation data containing respective evaluation values of a plurality of index items, each index item is related to an exercise function of a user,
generate a training menu based on the analysis evaluating data, the training menu indicating one or more training tasks for the finger exercise to be completed by the user,
store training menu data in the memory, and
display the training menu to the user on a screen of a display,
wherein each index item includes an amount of exercise, an endurance, rhythmicity, cooperativeness of both fingers, and marker trackability,
wherein the memory stores a plurality of training items that respectively correspond with the plurality of index items and indicate one or more training tasks for improving the respective index items, the training items include an exercise task to perform finger tapping in accordance with teaching information, stimulation, or marker tracking,
wherein the training items include, as parameters, pace, duration time, and a hand to be used, the parameters having respective parameter values,
wherein the processor is further configured to:
select a plurality of index items, which include an index item whose evaluation value is relatively low among the evaluation values based on a predetermined condition,
select a plurality of training items associated with the selected index items,
generate the training menu for improving the selected index items by using the selected training items, and
when the training menu is generated, generate a combination of the selected training items based on a first combination depending upon a permutation of the selected training items or a second combination that is not dependent upon a permutation of the selected training items, and generate the training menu including plural kinds of training that correspond to the first combination of the training items or the second combination of the training items, and
wherein the plural kinds of training in the training menu are arranged and displayed in an order from training of a single training item for improving a single index item to training of a plurality of training items for improving the first combination or the second combination of a plurality of index items.

2. The finger exercise training system according to claim 1, wherein the processor is further configured to:
present a task for the finger exercise to the user, and measure the finger exercise of the task carried out by the user, and
extract a feature amount based on the measured data, execute an analysis evaluating process to calculate the evaluation values of the index items based on the feature amount, store the analysis evaluating data, and display an evaluation screen on the display based on the analysis evaluating data before the user performs the training, the evaluation screen including the evaluation values of the index items.

3. The finger exercise training system according to claim 2, wherein the measured data is first measured data obtained by the processor before the user performs the training,
wherein the processor is further configured to:
obtain second measured data and store the second measured data in the memory, the second measured data is data from a finger exercise of the training that is performed by the user in accordance with the training menu,
execute analysis evaluating process based on the second measured data to obtain second analysis evaluation data, the second analysis evaluation data containing respective evaluation values of the plurality of training items corresponding to the training items of the generate training menu, and display a training result screen indicating the evaluation values of the index items based on the second analysis evaluation data.

4. The finger exercise training system according to claim 3, wherein the processor is further configured to: manage user information, the user information containing history information of actual results of past training of the user, and wherein the processor is further configured to determine an index item whose evaluation value is relatively low based on the training item of the training menu data for a previous training of the user and an evaluation value of the index item of the analysis evaluation data after the previous training, and generate a training menu for training by using the training item to improve the determined index item.

5. The finger exercise training system according to claim 2, wherein the feature amount contains at least one of a distance between two fingers on the finger tapping, speed, acceleration, a tap interval, a phase difference between both hands, or a delay time of marker tracking.

6. The finger exercise training system according to claim 1, wherein the processor is further configured to: register user information, the user information containing attribute values including sex, age, and a disease of the user, and select the training items in accordance with the attribute values of the user or adjust a detailed parameter value of the training item upon creating of the training menu.

* * * * *